United States Patent [19]
Bullard et al.

[11] Patent Number: 5,851,188
[45] Date of Patent: Dec. 22, 1998

[54] DEVICE FOR HOLDING MEDICAL INSTRUMENTATION SENSORS AT AND UPON THE CERVIX OS OF A HUMAN FEMALE, PARTICULARLY FOR HOLDING THE ULTRASONIC TRANSDUCERS OF AN ULTRASONIC TRANSIT TIME, REAL-TIME, CERVICAL EFFACEMENT AND DILATATION MONITOR

[76] Inventors: Kelli M. Bullard; Michael Harrison, both of c/o UCSF Fetal Treatment Center 1661 Health Sciences West 3rd & Parnassus, San Francisco, Calif. 94143; W. Scott Kemper, 3334 Buena Vista St., San Diego, Calif. 92109; Michael P. Guberek, 426 Jolina Way, Encinitas, Calif. 92024

[21] Appl. No.: 512,333

[22] Filed: Aug. 8, 1995

Related U.S. Application Data

[63] Continuation-in-part of Ser. No. 322,613, Oct. 12, 1994, Pat. No. 5,438,996.

[51] Int. Cl.[6] .................................................... A61B 8/00
[52] U.S. Cl. ........................ 600/448; 600/588; 600/591
[58] Field of Search ..................... 128/660.01, 660.02, 128/660.06, 661.02, 662.03, 662.06, 675, 774, 775, 778, 832, 841; 600/437, 438, 442, 448, 459, 462, 488, 587, 588, 591

[56] References Cited

U.S. PATENT DOCUMENTS

| 4,200,090 | 4/1980 | Drobish ................................... 128/832 |
| 4,517,970 | 5/1985 | Goepp et al. ........................... 128/841 |
| 4,589,880 | 5/1986 | Dunn et al. .............................. 128/832 |

*Primary Examiner*—George Manuel
*Attorney, Agent, or Firm*—Fuess & Davidenas

[57] ABSTRACT

A flexible elastomeric annulus-shaped membrane having a shape-retentive memory and exerting a force so as to assume and to maintain a predetermined closed-loop geometric shape, normally a circle, fits circumferentially about the cervix os of a human female so as to hold and retain medical instrumentation probes, preferably two opposed wire-connected ultrasonic transducers of a real-time transit-time ultrasonic monitor of cervical dilatation and effacement. The annular membrane may optionally extend as a tube downwards in the vaginal canal, in the manner of a female diaphragm, as to shield the wires from the walls of the vagina. The membrane expands and contracts with such cyclical variation in the dilatation and effacement of the cervix os as occurs from the earliest onset of labor until imminent childbirth. The membrane holding the transducer probes of an ultrasonic cervimeter may be situated in place about the cervix os for prolonged periods ranging to several months, or may be placed only at the onset of full labor, for monitoring purposes.

14 Claims, 19 Drawing Sheets

ADVANTAGES AND DISADVANTAGES OF DIGITAL CERVIMETRY METHODS

| | Digital Cervimetry | Mechanical Cervimetry | Magnetic Cervimetry | Previous Ultrasonic Cervimetry | Present Invention Cervimetry |
|---|---|---|---|---|---|
| Installation | Easy | Difficult | Difficult | Difficult | Difficult |
| Patient comfortable during installation | No | No | No | No | No |
| Patient comfortable after installation | Yes | No | Yes | Yes | Yes |
| Convenience | High | Low | Moderate | Moderate | High |
| Measurement by Stretching | Yes | Yes | No | No | No |
| Possibility of Digital Pelvic Examination | Yes | No | Diminished | Diminished | Slightly Diminished |
| Output Stability | Subjective | Calipers moveable (1) | Relies on signal intensity (2) | Relies on signal transit time; good | Relies on signal transit time; good |
| Output Linearity | Subjective | Yes, almost | Yes (3) | Yes | Yes |
| Recording up to full dilatation | Yes | No; limited (4) | Not always (5) | Yes | Yes |
| Patient Ambulatory | No | No | No | No | Yes |
| Monitoring, with History | No | No | No | Limited | Total |
| Monitoring, with Alarm | No | No | No | Yes | Yes |

Figure 1

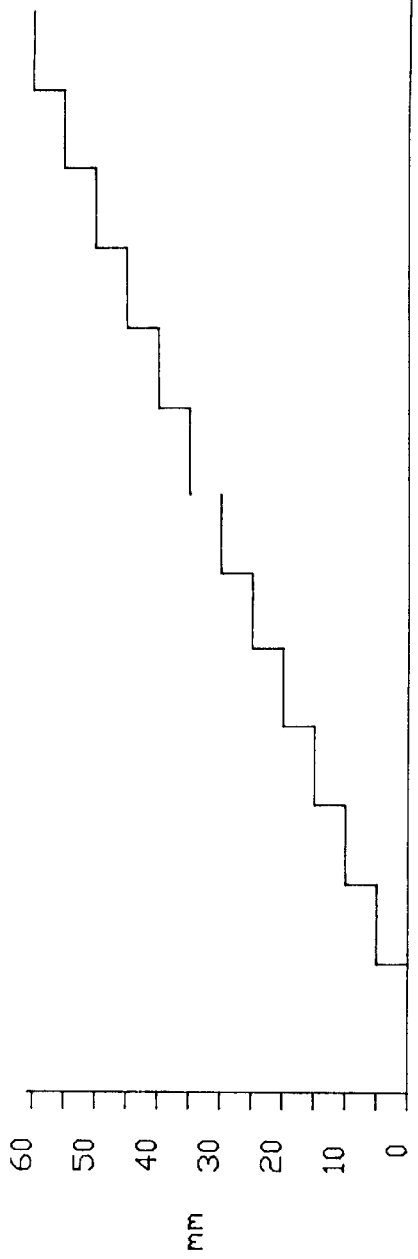
Fig. 5a CALIBRATION
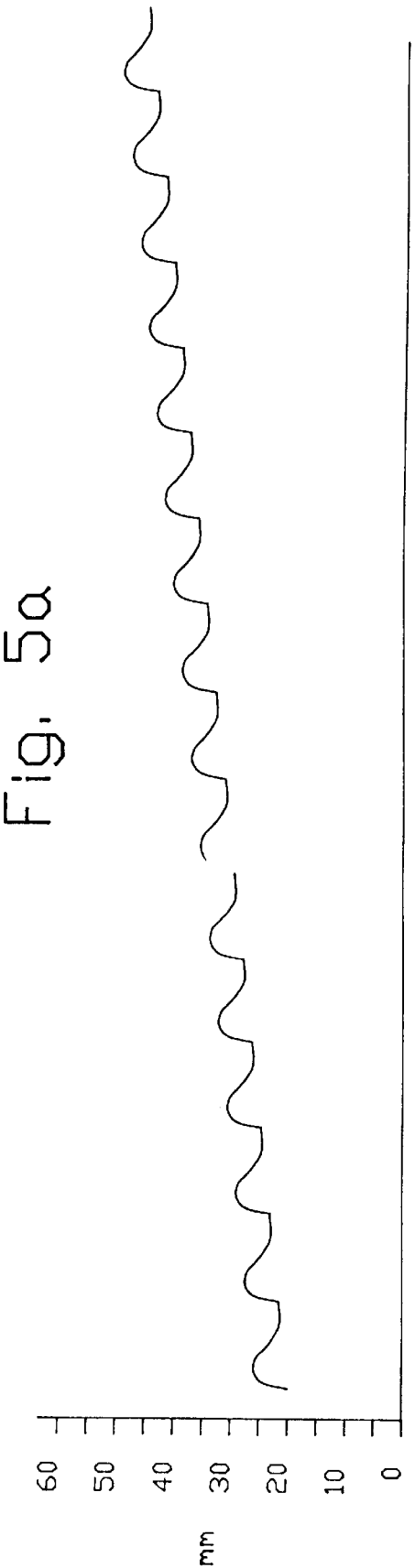
Fig. 5b CERVICAL DIAMETER

DEVICE FOR HOLDING MEDICAL INSTRUMENTATION SENSORS AT AND UPON THE CERVIX OS OF A HUMAN FEMALE, PARTICULARLY FOR HOLDING THE ULTRASONIC TRANSDUCERS OF AN ULTRASONIC TRANSIT TIME, REAL-TIME, CERVICAL EFFACEMENT AND DILATATION MONITOR

REFERENCE TO RELATED APPLICATIONS

The present application is a Continuation-in-Part of U.S. patent application Ser. No. 08/322,613 filed Oct. 12, 1994, for an AMBULATORY, ULTRASONIC TRANSIT TIME, REAL-TIME, CERVICAL EFFACEMENT AND DILATATION MONITOR WITH DISPOSABLE PROBES issued Aug. 8, 1995, as U.S. Pat. No. 5,438,996. This predecessov application and patent is to the selfsame inventors W. Scott Kemper and Michael P. Guberek who are among the co-inventors of the present application.

The present application is a companion to U.S. patent application Ser. No. 08/514,234 for a SYSTEM AND METHOD FOR THE INFUSING OF TOCOLYTIC DRUGS IN RESPONSE TO THE ONSET OF PREMATURE LABOR DETECTED BY ULTRASONIC MONITORING OF THE DILATATION AND/OR EFFACEMENT OF THE CERVIX OS filed on an even date herewith. The related application is to inventors including the selfsame Michael Harrison, W. Scott Kemper and Michael P. Guberek who are among the co-inventors of the present application.

The contents of the predecessor and of the companion patent applications are incorporated herein by reference.

BACKGROUND OF THE INVENTION

1. Field of the Invention

The present invention generally concerns devices for holding medical instrumentation probes at an in contact with the cervix os of a human female.

The present invention particularly concerns non-penetrating elastomeric devices that hold position at and about the cervix of in order to hold the probes of medical instrumentation in position at the cervix even during such periodic dilation and effacement thereof as are in advance of the onset of, and during, labor, particularly including, but not limited to, the ultrasonic transducers of an ultrasonic transit time, real-time, cervical effacement and dilatation monitor (being a type of cervimetry and cervimeters such as uses ultrasound as a basis of measurement).

2. Description of the Prior Art

Although the present invention will be seen to be quite general in application for holding medical instrumentation probes at and on the cervix os of the human female, one particular, preferred embodiment of the invention will seen to be particularly adapted (i) for holding a pair ultrasonic transducers, while, and nonetheless to, (ii) any periodic dilation (and, alternately cyclically, constriction) and cyclical effacement of the cervix os in advance of the onset of labor. This particular embodiment is intended for use with the ultrasonic transducers of an ultrasonic cervical effacement and dilatation monitor, including a monitor that is transit time, real-time, and/or ambulatory.

The use of such a transducer probe holder, and such a ultrasonic cervical monitor, in the present and in the related inventions is directed to the avoidance of spontaneous abortion and premature labor, and the prolongation of gestation, in human females. Gestation is desirably prolonged for variously increasing minimum periods in order to (i) make more probable a viable live birth, (ii) reduce the incidence of health complications attending a prematurely born child, and (iii) reduce the time period during which a premature infant, even if healthy, must, because of its size and viability, receive extraordinary care. All the factors of (i) live birth, (ii) a healthy child, and (iii) a child that can timely leave the hospital in the custody of its parents, obviously have an impact on the happiness and well-being of the parents and relatives. There is also and impact on society, including a very great societal economic impact in caring for children delivered greatly prematurely.

Fortunately, there is a class of drugs call tocolytic, or labor-preventing, drugs that are effective to postpone labor if, and only, if administered before the full onset thereof. These drugs have undesirable side effects, and cannot be continuously administered to a pregnant woman during the duration, or even during the high risk period, of a her pregnancy. It is necessary to (i) timely detect the early onset of labor, and (ii) timely administer a tocolytic drug, if labor is to be avoided, and pregnancy prolonged. As will be further discussed, the cyclical dilatation and effacement of the cervix os of a gravid female appears, circa 1995, to be a useful and non-invasive way of detecting the early onset of labor in mammals, including humans.

The record short human gestations which have resulted in viable live births are, circa 1995, twenty-six (26) weeks. These exceptionally rare survivals are the subjects of papers in medical journals. The normal period considered the practical minimum for gestation if a live birth is likely realizable in a major medical center is twenty-eight (28) weeks. If the birth transpires in a facility without specialized facilities for the care of premature infants, or in areas of the second or third world where childbirth becomes progressively more hazardous for both the mother and child, the period during which the child is desirably maintained in utero increases all the way to normal full term. Human gestation is desirably extended to thirty-four (34) weeks in order to assure near-normal probability of a viable live birth even under the best, first-world, circumstances. Although the probability of successful delivery, and the good health of the newborn continues to improve (sometimes for reasons more reflective of the overall good health and prenatal care of the mother as opposed simply to the benefit of being longer in the womb) all the way up to the normal full human gestation period of thirty-six to forty (36–40)weeks, active medical intervention is normally not used to postpone labor beyond thirty-four (34) weeks.

Accordingly, human gestation is, if possible and other medical conditions of the pregnant woman not counter-indicating, preferably prolonged as long as about thirty-four (34) weeks, which is considered the lower limit for live birth in advanced modern facilities without appreciably greater complications than are incurred by babies carried to the full normal term of thirty-six to forty (36–40) weeks. If gestation can be prolonged from the practical minimum of twenty-eight (28) weeks at which viable live births routinely transpire in advanced hospitals for only four (4) weeks longer, i.e., to thirty-two (32) weeks, then a cost savings in excess of $100,000 to $300,000 U.S. can typically be realized circa 1995—even over the costs of continuous hospitalization and monitoring of the mother during the critical period. It should be understood that there are some areas of the United States, and most of the world, where neither the quality nor the quantity of resource exists to keep a highly premature infant alive. Although direct financial outlays may be less in these areas, the human cost is very great. People inevitably wishing to have children, and there being no viable way to even certainly detect, let alone prevent the pregnancies of, females at risk for premature delivery, it is thus of consummate interest to prolong, if possible, pregnancies until (usually) near full term.

Cause and constant supervision of high-risk pregnancies has historically involved the use of what were, at the times introduced, new and advanced technologies. This lengthy background has led, culminating in the present and related inventions, to the continuous recording and monitoring of cervical dilatation during labor by means of ultrasonic cervimetry. To support this continuous monitoring, probes must be maintained continuously in position.

The ancients knew that the dilatation of the cervix, discernable with and by the fingers during manual digital assessment, attended the onset of labor in the human female.
2.1 The General History of Cervimeters Including Ultrasonic Cervimeters, and of the Measurements Obtainable With Such Cervimeters Current medical knowledge of cervical behavior descends largely from a huge base of historical data obtained by repeated digital palpation or 'digital cervimetry' during labor. Both vaginal and rectal examination have been used. The latter method was introduced by Kroenig to prevent ascending uterine infection. Reference Kroeig, A. . Der Ersatz der inneren Untersuchung Kriessender durch die Unteersuchung per Rectum; CENTRALBL GYNAKOL 1894; 18:235–243. Semmelweiss' classic work involving the relationship between vaginal examination and puerperal infection is well appreciated. Reference Semmelweiss, I., in Von Gorky, Y., ed., Semmelweisss gesammte Werke, Jena. 1905, VEB Gustav Fisher Verlag.

Although digital examination offers valuable clinical information on the progress of labor, its intermittent character does not allow an assessment of the dynamics of cervical dilatation. For that reason many attempts have been made to construct devices, cervimeters, for objective and continuous measurement of cervical dilatation based on (electro) mechanical, electronic and ultrasonic principles. A historical overview of some of nineteen various instruments published since the early fifties is presented in the article Assessment of cervical dilatation during labor; a review, by T. vand Dessel, et al. appearing in EUR. JNL. OBS. GYN. & REP. BIO. 41 (1991) 165–171.

Instrument-based cervimetry, or cervical dilatation measurement, has in particular been performed by mechanical, magnetic and/or ultrasonic means. A history of instrument-based cervimetry is presented by Moss, P. L., et al. as Continuous cervical dilatation monitoring by ultrasonic methods during labor, appearing in AM. J. OBSTET. GYNECOL. 132:16, 1978. The following text is derived from that article.

Moss, et al. point out that Friedman was the author in 1936 of a report discussing mechanical cervimetry. See Friedman, E. A.: Cervimetry, an objective method for study of cervical dilatation in labor, AM. J. OBSTET. GYNECOL. 71:1189, 1956. This paper was followed by another paper co-authored with Von Micsky in 1963. See Friedman, E. A., and Von Micsky, L. I.: Electronic cervimeter, A research instrument for the study of cervical dilatation in labor, AM. J. OBSTET. GYNECOL. 87:789.

Siener cooperated with West from 1962 to 1972, and with Krementsoy in 1968, in the use the same method. See Siener, H.: An apparatus for recording the opening of the cervix during labor, ZENTALBL GYNAEWKOL 78:2069, 1956; Siener, H.: A new electromechanical apparatus for measuring labor activities by the execution of combination measurements, ARCH. GYNAEKOL. 196:365, 1961; Siener, H.: First stage of labor recorded by cervical tonometry, AM. J. OBSTET. GYNECOL. 86:303, 1963; Siener, H. and West, I.: Internal isometry and graphic registration of cervix dilatation as a basis for calculation of labor effectiveness and soft tissue resistance, GEBURTSHILFE FRAUENHEILKD 32:123. 1972; and Krementsoy, U.: Improved technique for measurement of cervical dilatation, BIOMED. ENG. (N.Y.) 2:350 1968.

The magnetic cervimeter was first proposed by Smith in 1954. See Smith, C. N.: Measurement of the forces and strains of labor and the action of certain oxytocic drugs, International Congress of Obstetrics and Gynecology, Geneva, 1954, S. A. George, P. 1030. However there were many drawbacks and it was only in 1971 that Rice, and also Kriewall, tried to solve these problems. Reference Rice, D. A.: Mechanism and measurement of cervical dilatation. Doctoral thesis, Purdue University, Lafayette, Indiana, 1974. Reference also Kriewall, T. J.: Measurement and analysis of cervical dilatation in human parturition, Doctoral theses, University of Michigan, Ann Arbor, Mich. 1974.

Ultrasonic cervimetry was introduced in the period from 1974 to 1976 by Neuman, Wolfson, and Zador. Reference Neuman, M. R. Wolfson, R. N. and Zador, I,: Ultrasonic transit time methods for monitoring the progress of obstetrical labor, TRANSACTIONS OF PROFESSIONAL GROUP ON ULTRASONICS—IEEE, Vol. 33, 1975; Zador, J.: Ultrasonic determination of cervical dilatation during labor, Master's thesis, Case Western Reserve University, Cleveland, Ohio, 1974; Zador, I, Neuman, M. R. and Wolfson, R. N.: Continuous monitoring of cervical dilatation during labour by ultrasonic transit-time measurement, MED. BIOL. ENG. 14–229, 1976; and Wallenburg, H. C. S., and Wladimiroff, J. W.: Ultrasonic measurement of cervical dilatation during labor, AM. J. OBSTET. GYNECOL. 126:288, 1978.

A comparison of the advantages and inconveniences of each prior art method is shown in the first four columns of the Table of FIG. 1.
2.2 Ultrasonic Cervimetry A typical advanced method of ultrasonic cervimetry, and the analysis of the measurements obtained thereby, was expounded by Moss, P. L., et al. in the aforementioned paper Continuous cervical dilatation monitoring by ultrasonic methods during labor, appearing in AM. J. OBSTET. GYNECOL. 132:16, 1978.

The major goal of Moss, et al., as stated in their own words, was to evaluate ultrasonic cervimetry and to look at the characteristics of the recordings with respect to conventional variables of fetal monitoring. In particular, Moss, et al. looked at the relationship between dynamic changes in cervical dilatation and intrauterine pressure. They looked at both the amplitudes of the changes and the phase relationships between the two signals.

The installation of the transducers consisted of fixing two piezoelectric crystals, each of dimension 1 mm by 5 mm, to the external os of the uterine cervix. The installation took place at 3 cm or more of dilatation. The crystals were fixed in places dramatically opposed to each other and were so held in position by spring-loaded clips.

The ultrasonic cervimeter in use generated an ultrasound wave each second, and the total time elapsed from the emission of that signal by one crystal to the reception by the other was compiled and converted into a distance. The ultrasound wave velocity was considered to be constant at 1.48 mm per microsecond. Since time, and not intensity, of the signal was the important parameter, the crystals had to rotate more than 60 degrees from one another before an error in the measurements was introduced. Migration was not possible since the clips teeth, when closed, pierced the cervix through and through.

The dilatation value along with the fetal heart rates, the fetal electrocardiograms, and the uterine contractions were recorded on an eight channel recorder.

Clinical accuracy was 0.6 cm. When the ultrasound recording of cervical dilatation is compared to the intrauterine pressure curve, it is characterized by a baseline and wave-shape curve of dilatation (DWP). The maximal amplitude component is called cervical maximal plasticity. The onset of the DWP is related to cervical resistivity, and the end of DWP reflects the relaxation time of cervical dilatation. The data show that as dilatation enters the active phase of labor, the plasticity, the resistivity, and the duration of relaxation of the cervix increase. These observations are related to the structural changes of the cervix during labor. (AM. J. OBSTET, GYNECOL. 132.16 1978).

It was noted by Moss, et al. (op. cit.) that cervical dilatation and fetal descent can be monitored simultaneously by ultrasound.

2.3 Problems With Previous Cervimeters—Mechanical and Electromechanical Cervimeters The analysis of this section 2.3, and of the following sections 2.4 and 2.5, is a substantial extract and paraphrase of the aforementioned article Assessment of cervical dilatation during labor: a review, by T. van Dessel, J. H. M. Frijns, F. Th. J. G. Th. Kok, and H. C. S. Wallenburg appearing in EUROPEAN JOURNAL OF OBSTETRICS & GYNECOLOGY AND REPRODUCTIVE BIOLOGY, 41 (1991) 165–171.

Two main prototypes of mechanical cervimeters have been described, the calipers-type and the string-type.

In the basic calipers-type cervimeter, X-cross calipers equipped with a centimeter rule at the distal end are used to measure the distance between opposing cervical rims. The Krementsov cervimeter, called an 'orificiometer' [18], has a ring at each proximal caliper end in which the fingers of the examiner can be placed. See Krememtsov, Y. G., Improved technique for measurement of cervical dilatation, BIOMED. ENGIN. 1968:2:350. It enables the examiner to verify his findings by vaginal examination. The Tervila cervimeter consists of two pairs of Kelly clamps, attached separately to the cervical edges, and connected in a hinge-like way. See Tervila, L., Measurement of cervical dilatation in labour, AM. J. OBSTET. GYNECOL. 1953;51:374–376. The Friedman cervimeter is equipped with bulldog clips for attachment to the cervical rims. See Freidman, E. A., Cervimetry: an Objective method for the study of cervical dilatation in labor, AM. J. OBSTET. GYNECOL. 1956;71:1189–1193. Measurement is continuous, but readings are obtained at 2 to 10 minute intervals and plotted manually against time.

Disadvantages of these simple mechanical cervimeters are the discontinuity of readings, the lack of recording facilities and the quite heavy mechanical construction that interferes with dilatation during measurement.

In later years, low-weight calipers with cervical attachment clips were combined with potentiometers to convert the movements of the caliper arms into an electrical signal that could be recorded on a polygraph. Electromechanical cervimeters of this basic type were described by Vossius, G. in Eine Methode zur guantitativen Messung der Erweiterung und des Tiefertretens des Muttermundes Wahrend der Geburt. Z GESAMTE EXP MED 1961;134:506–512, by Svoboda, M. in CSL. GYNAEKOL 1958;23:621–623, cited by Warm R., Ueber die Messung der Muttermundseroffnung unter der Geburt. Z Arztl Fortbild 1967;61:661–666, by Richardson, J.Aa, Sutherland, I. A., Allen D. W., and Dore F., in The development of an instrument for monitoring dilatation of the cervix during labour; BIOMED. ENGIN. 1976;11:311–313, and by Richardson J. A., Sutherland I. A.; Measurement of cervical dilatation during labour; Physical science techniques in obstetrics and gynecology, Tunbridge Wells: Pitman Medical, Kent, United Kingdom, 1977. In the paper The electromechanical Friedman cervimeter by Friedman, E. A., and Von Micsky, L. I., an electronic cervimeter is taught as a research instrument for the study of cervical dilatation in labor. Reference AM. J. OBSTET. GYNECOL. 1963;87:789–792. The Freidman electronic cervimeter is attached to the cervix by a retractable row of needles. At a preset dilatation the needle attachments to the cervix are automatically released. In another instrument developed and expounded by Langreder, W. in Geburtshilfliche Messungen, BIBL. GYNAECOL 1965;20 (S), movements are recorded by means of a photoelectric cell. The cervimeters described by Warm, R. in Ueber die Messung der Muttermundseroffnung unter der Geburt. appearing in Z. ARTZL FORTBILD 1967;61:661–666, and by Kazda S. Brotanek V. in Part played by cervix in uterine activity at the onset of labour appearing in CSL. GYNAEKOL 1962;27:333–337, have a similar design. A pair of calipers is connected to an invisible hinge in a heavy extravaginal part containing an internal potentiometer. Kazda and Brotanek report successful recordings in 90 patients without presenting data.

Siener has reported several cervimeters. The original Siener cervimeter was reported by Siener H., Ein neues elektromechanisches Wehenmessgerat zur Durchfuhrung von Kombinationsmessungen, ARCH. GYNAKOL 1961;196;365–372, by Siener H., First stage of labor recorded by cervical tonometry; AM. J. OBSTET. GYNECOL. 1963;86:303–309, by Siener H. and Wust L., Innere Wehenmessung and graphische Registrierung der Muttermunds-Eroffnung als Grundlagen zur Berechnung der Weheneffektivitat und des Weichteil-widerstandes; GEBURTSH FRAUENHEILK 1972;32:125–130. It was also reported by Embrey M. P. and Siener, H. Cervical tocodynamometry; J. OBSTET. GYNAECOL. BRIT. COMMONW. 1965;72:225–228, and in Siener H., Cervical dynamometry, a new method in obstetrical research; Am. J. OBSTET. GYNECOL. 1964;89:579–582. The Siener cervimeter offers the opportunity for both measurement of cervical dilatation and measurement of cervical dilatation forces, after fixation of the calipers. Later Siener used the concept of the electromechanical calipers cervimeter to construct even more sophisticated devices: the cervical dynamometer and the 'erweiterte Zervixwehenmesser' ('expanded cervix-contraction meter'). Reference Siener H., Die erweiterte Zervixwehenmessung; GEBURTSH FRAUENHEILK 1959;19:140–145. The cervical dynamometer allowed measurement of the pressure of the fetal head on the cervix after fixation of the intravaginal arms of the cervimeter. The 'expanded cervix-contraction meter' combined a calipers cervimeter with a metal construction for measurement of fetal descent.

The string-type cervimeter consists of strings or cords, attached to the cervix. Changes in dilatation cause changes in length of the strings which are transmitted to a kymograph by a mechanical pulley-guided system. Reference Siener H., Studien uber das Verhalten des Muttermundes wahrend der Eroffnungsperiode; ARCH. GYNAEKOL 1957;118:556–576. Alternatively, the changes could be electrically communicated by a linear differential transformer.

Reference Smyth C. N., Measurement of the forces and strains of labour and the action of certain oxytocic drugs. Comptes Rendus du Congres International de Gynecologie et d'Obstetrique, Geneva, 1954;1030–1039.

Some instruments are described for assessment of cervical properties other than dilatation. Glass and coworkers has used the medical engineering principle of indentation to design an electromechanical device for measurement of the relative softness of the cervix. Reference Glass B. L., Munger R. E., Johnson W. L.; Instrument to measure tissue softness of the uterine cervix in pregnancy; MED. RES. ENGIN. 1968;7:34–35. An instrument to measure the amount of pressure of the fetal head on the cervix has been reported by Noack and Blaschkowski. Reference Noack H. and Blaschkowski E., Zur Frage der graphischen Registrierung von Kontraktionen des Muttermundes unter der Geburt; Z. GYNAKOL 1958;80:160=–1616.

Mechanical cervimeters are cumbersome in clinical practice and they cannot be used for continuous measurement of dilatation. Most electromechanical devices offer the possibility of continuous registration but have the disadvantage of a mechanical intravaginal part, which may interfere with cervical dilatation.

2.4 Problems With Previous Cervimeters—Electromagnetic Cervimeters

Electromagnetic cervimeters were described by Wolf in a his congress report: Wolf W., Kongressbericht. ARCH. GYNAKOLOGIE 1951;180:177–180; and later by Rice, D. A. in Mechanism and measurement of cervical dilatation; Doctoral dissertation. 1974, Purdue University, Lafayette, Ind. U.S.A. With these cervimeters cervical dilatation is measured using two small induction coils, attached to opposing cervical rims. An electrical current, sent through one of the coils, establishes a magnetic field that is detected in the opposite coil and then recorded. Kriewall has used a permanent magnet dipole as a magnetic field source and two Hall-effect magnetic-field transducers as detectors. Reference Kriewall, T. J., Measurement and analysis of cervical dilatation in human parturition; Doctoral thesis, 1974, University of Michigan, Ann Arbor, Mich., U.S.A. The signals derived with this technique are processed to determine the distance between the transducers.

Electromagnetic cervimeters with clinical applicability have not been described.

2.5 Problems With Previous Cervimeters—Ultrasound Cervimeters

Abdominal routes have been used to visualize cervical dilatation by means of ultrasound during pregnancy. Reference Sarti D. A., et al. Ultrasonic visualization of a dilated cervix during pregnancy; RADIOL. 1979;130:417–420; Varma T. R., Patel R. H., and Pillai U. Ultrasonic assessment of cervix in normal pregnancy; ACTA. OBSTET. GYNECOL. SCAND. 1986;65:229–233; Parulekar S. G. and Kiwi R., Dynamic incompetent cervix uteri; J. ULTRASOUND MED. 1988;7:481–485.

Vaginal routes have been used to visualize cervical dilatation by means of ultrasound during pregnancy. Reference Balde M. D., Stolz W., Unteregger B., and Bastert G.; L'echographie transvaginale, un rapport dans le diagnotic de la beance du cal uterin; J. GYNECOL. OBSTET. BIOL. REPROD. (Paris) 1988;17:629–633

Transperineal routes have been used to visualize cervical dilatation by means of ultrasound during pregnancy. Reference Lewin B., L'echotomographie perineale. Une nouvelle methode de mesure objective du cal; J. GYNECOL. OBSTET. REPROD. 1976;5:289–295; and Jeanty P., Perineal scanning; AM. J. PERINATOL. 1986;3:289–295

Reports in the literature dealing with systematic visual assessment of cervical dilatation during labor could not be found by T. van Dessel, et al. (op. cit.), nor by Applicants.

A different approach uses two ultrasound transducers attached to opposing rims of the cervix. An ultrasonic signal generated by one transducer is received by the opposing one. Since the ultrasound velocity is known, the transmission time allows computation of the distance between the transducers.

The first ultrasound cervimeter was described by Zador et al. in 1974. Reference Zador, I, Neuman, M. R., and Wolfson, R. N.; Continuous monitoring of cervical dilatation during labour by ultrasonic transmit-time measurement; MED. BIOL. ENGIN. 1976;14:299–305; also Zador, I, Wolfson R. N., and Neuman, M. R., Ultrasonic measurement of cervical dilatation during labor; ANN. CONF. ENGIN. MED. BIOL. 1974;16:187. These authors used spring-loaded clips to attach the transducers to the cervix. A total of 24 readings of women in labor were reported, but no specific data were given. Apparently, practical problems were encountered, because further clinical studies with this device could not be found.

A similar cervimeter has been presented by Kok et al. in 1976 in preliminary reports. Reference Kok, F. T., Wallenburg, H. C., and Wladimiroff, J. W., Ultrasonic measurement of cervical dilatation during labor; AM. J. OBSTET. GYNECOL. 1976;126:288–290; also Eijskoot, F., Storm, J., Kok, F. T., Wallenburg, H., and Wladimiroff, J.; An ultrasonic device for continuous measurement of cervical dilatation during labor; ULTRASONICS 1977;55:183–185. The problems with the fixation of the transducers to the cervix were eliminated by using special spiral-shaped transducers. The data was analyzed off-line by a computer, and accuracy and precision in vitro and in vivo were shown to be good in a well-documented study of 62 women in labor. Reference Kok, FTJGT; Ultrasonic cervimetry (summary in English); PhD-Thesis, Erasmus University, School of Medicine and Health Sciences, Rotterdam, 1977.

Cervical dilatation appeared to follow a wave pattern reflecting the intrauterine pressure curve. Maximal cervical dilatation coincided with the maximal intensity of each contraction. Generally, the derived curve of cervical dilatation showed the sigmoid shape postulated by Friedman (op. cit.) and by Krementsov Y. G. in Improved technique for measurement of cervical dilatation; BIOMED. ENGIN. 1968;2:350. A decelerative phrase was never detected. Using a similar device Moss and coworkers have investigated 13 women in labor. Reference Moss P. L., Lauron P., Roux J. F., Neuman M. R., and Dmytrus K. C.; Continuous cervical dilatation monitoring by ultrasonic methods during labor; AM. J. OBSTET. GYNECOL. 1978;132:16–19. T. Van Dessel, et al. (op. cit.) observed—contrary to the findings reported by Kok, Zador I, Neuman M. R., Wolfson R. N. in Continuous monitoring of cervical dilatation during labour by ultrasonic transmit-time measurement. MED. BIOL. ENGIN. 1976;14:299–305—that the peaks of uterine contraction and cervical dilatation were out of phase.

Ultrasound visualization of the cervix may be helpful in monitoring the patient at risk for premature delivery, but does not allow continuous registration of dilatation during labor. However, ultrasonic cervimetry does offer continuous and reliable recording with little discomfort to the patient, but clinical data has been limited. T. van Dessel, et al., (op. cit.) felt in 1991 that "[u] ltrasound cervimetry may be a useful research tool for the study of the cervical response to the uterine contractions during labor. For clinical obstetric purposes, however, digital assessment of cervical dilatation seems sufficient."

2.6 Problems With Previous Ultrasonic Cervimeters—Position-holding of Placed Probes In the predecessor patent application it is taught that ultrasonic transducers to which various barbs of the order of corkscrews to fish hooks are affixed may be reliably semi-permanently affixed to the cervix os, which is devoid of nerve endings. The fact that the placement of these vicious-looking devices may benefit the patient without inducing pain or harm—much in the manner of the similarly-appearing corkscrew probe of a cardiac pacemaker—does little to assuage the sensitivities of the female in whose birth canal these devices are to be affixed.

Especially since the ultrasonic probes are generally to be maintained in position for a prolonged period ranging to many months while the carrier female is conscious, and because the carrier female must be able to recognize a probe should it come loose and become resident in, or become ejected from the vaginal canal, the patient should be shown the probe and its affixation means, and its function and operation should be explained to the patient, and should be understood by the patient.

The present invention will be seen to be directed to a more psychologically-user-friendly placement and holder device for cervical instrumentation, including a pair of ultrasonic transducer probes as may be used with a cervical dilatation and effacement monitor.

2.7 The Desirability of Continuous Accurate Convenient Cervical Dilation/effacement Monitoring, With Automated Alarms The inventors of the present invention are of a contrary opinion to the opinion of T. van Dessel, et al., (op. cit.) in the aforementioned paper that "digital assessment of cervical dilatation . . . [is] sufficient" and that, by implication, ultrasound cervimetry has no role in the clinical environment.

In the first place, the only realistic alternative to ultrasonic cervimetry is, and has proven to be, no cervimetry at all, and exclusive reliance the time-honored approach of digital assessment of cervical dilatation. This procedure, which should be, and regularly is, performed every hour after the onset of labor, is (i) manifestly inadequate to detect the onset of labor itself, (ii) laborious, (iii) without automatic contemporaneous generation of a permanent record, and (iv) of no greater quality in results obtained than the skill and attentiveness of the practitioner.

Despite the lack of clinical, or patient portable, instrumentation for the detection of the onset of labor (should such event be sharply definable, and it is), the detection of this event is very important in those rare cases where premature labor must be avoided. The inventors of the present invention are involved in the verification of instrument with one of the major centers for the management of problem pregnancies and premature births in the United States if not also the world circa 1994. Prolongation of gestation beyond a certain, threshold, number of weeks is currently very, even crucially, important to the survival of the fetus at birth. This minimum gestation period for live birth has greatly decreased in recent years, but cannot be expected to decrease to shorter than the period within which spontaneous abortions, or premature labor, occur in the human female. Accordingly, the only way that some fetuses will ultimately be viable is if tenure in the womb is prolonged.

Powerful drugs exist to arrest labor. However, these drugs cannot be continuously, or even regularly administered, during the projected terminal phase (at whatsoever period gestation) of a particular problem pregnancy. Accordingly, it is of crucial importance to detect the onset of labor (should such event be detectable, and it is) at the earliest possible moment in order that it may be stopped, if desired or required, by the administration of drugs or otherwise.

Next, once labor has begun, and even in normal pregnancies and deliveries, the inventors of the present invention do not take such a cavalier attitude as do their peers to the present lack of hard, recorded, and/or instantaneous quantitative data about what has gone on, and is going on, from moment to moment during labor. The dilatation/effacement of the cervix is a very good indicator of the progress, and or of problems, with labor.

2.7.1 Timing of Therapeutic Regimens Based in Cervical Dilation/Effacement Monitoring The first, and potentially greatest, advantage to the continuous monitoring of cervical dilatation/effacement during labor, if not also in the period before, is that it can promote superior timing in the administration of medical therapies to support the suppression of labor or during labor. Cervical dilatation/effacement monitoring promotes the timely and optimally timed therapeutic administrations in consideration of (i) the earliest possibly recognition of changing conditions, including problem conditions, during labor, (ii) a definitive record of exactly how long certain conditions have persisted, and (iii) the possibility of machine aids, ranging from alarms to the comparison of profiles to mathematical modeling.

In short, the fact that most births occur normally even should the midwife or obstetrician be ignorant of cervical dilatation, and the complementary fact that some births encounter problems, are both facts of nature, and not of man. However, the fact that intervention in the birth process, primarily by Caesarian section, is occasionally ancient and generally successful does not invariably mean that it has been optimally timed for the health of the fetus and/or the mother.

Timing in the administration of therapeutic regimens during labor has always been recognized to be an issue. For example, the administration of pain-killing drugs to the mother is permissible during the early stages of labor whereas the administration of the same drugs becomes impermissible in later stages of labor. For example, a Caesarian delivery is not normally attempted until some lapse of reasonable progress towards a normal, vaginal, delivery. The questions that should be asked by a clinical practitioner in considering the efficacy of a monitor device in accordance with the present invention are these: Is there any evidence that the timing of some (or any) interventions is more critical than the timing of other interventions, or more critical than is generally recognized, or, God forbid, more critical that is generally possible under current methods for the measurement of the progress of labor? If so, what interventions would so benefit? Finally, is the monitoring of cervical dilatation and/or effacement (the thinning of the cervical rim, which thinning is of course proportional to the expansion of the cervix) an appropriate, or useful, measure of the progress, and/or the onset of problems, during labor? The present specification does not contain proof that the answers to the first and the third questions are yes, nor need it do so. However, such data from clinical trials as is still under development circa April, 1994, suggests that this "yes" answer.

The present invention does not concern the medical diagnosis of problems during delivery, which is part of the evolving medical art of obstetrics. The present invention does concern, however, new machines and methods for the comprehensive measurement and display of, and the generation of alarms from, cervical dilatation/effacement during labor.

2.7.2 The Communication of the History of a Birth Based in Cervical Dilation/Effacement Monitoring The oral record and the written does not suffice for the communication of the stages, and circumstances, of complicated labor. The hard-copy, graphical, record of a continuous monitoring of cervical dilatation/effacement during labor can promote a number of ends. It permits the ready visualization of the progress of the labor. It permits all temporal junctures at which therapies were administered to be identified, and the results of these therapies (insofar as affecting cervical dilatation/effacement) recognized. It permits the ready communication of a history of the labor to (i) students, (ii) history, (iii) medical review boards and courts, and (iv) other physicians, including those who may attend other labors of the same female some years hence.

2.7.3 Diligence in Childbirth Monitoring Based in the Monitoring of Cervical Dilation/Effacement Childbirth in humans is a lengthy process which can commence totally asynchronously with the other duties and schedule of an attending obstetrician or midwife. The attentiveness of personnel attending to the labor can sometimes languish over the long periods involved. It is equally as undesirable that these personnel should be overly zealous. It is (i) difficult, (ii) unreasonable on the basis of medical results obtained, (iii) and more disturbing than beneficial to the patient, that a physician or attending midwife should be making excessively frequent manual digital assessment of the dilatation of the cervix during labor.

Accordingly, manual assessment of cervical dilatation during labor that is either too infrequent, or too frequent, is avoided. However, there is a fair amount going on in the cervical dilatation on a time scale that is short, and thus insufficiently captured, relative to even the most frequent manual digital assessment. Namely, this dilatation is cyclic on a time scale of typically from one (1) to two (2) minutes, as will be shown in this specification. Moreover, there is no desire to delay the recognition of changes, especially such changes as may be significant, simply because they do not coincide with the periodic, and likely infrequent, schedule of manual digital assessment.

In most labors and deliveries, including those that have problems, observational vagaries as may result in (i) imprecision and/or (ii) untimeliness in detection/measurement of the dilatation/effacement of the cervix the are of no consequence. The challenge is with those few difficult, often premature, labors and deliveries in which the timeliness and quality of information may be, or become, critical. In episodes of labor of this sort the physician faces a dilemma. His continuing observational interventions may precipitate the very events that he/she seeks to avoid. Conversely, optimal intervention may be compromised if the physician is not in possession of the most timely and accurate information.

Accordingly, a system that would continuously, accurately and reliably monitor cervical dilatation/effacement during labor without substantial discomfort, inconvenience, disturbance or hazard to the patient would be very desirable. The present invention concerns such a system.

SUMMARY OF THE INVENTION

The present invention contemplates a flexible annulus-shaped membrane having a shape-retentive memory and exerting a force so as to assume and to maintain a predetermined closed-loop geometric shape, normally a circle, circumferentially about the cervix os of a human female. In this position the membrane holds and retains one or more medical instrumentation probes, preferably two opposed wire-connected ultrasonic transducers of a real-time transit-time ultrasonic monitor of cervical dilatation and effacement.

The annular membrane may particularly be made from elastomeric material, preferably surgical latex. Both the exterior and interior circular circumferential regions of the annulus are preferably somewhat thickened, and in the form of an integral rings having a shape-retentive memory. However, whereas the exterior ring is substantially stable, exerting a continuous pressure force to assume and retain its base dimension and circular shape over an indefinitely long period, the interior ring will assume over time, at body temperature, and upon expansion of the cervix os a slight "set", and will stretch if required to ever larger dimensions. In this manner the annular membrane will not only cycle about the instant base dimension of the cervix os—should it be called upon to do so—but will never become so restrictive so as to, for example, hold closed the cervix in the manner of a pessary. The preferred annular membrane is never "tight", but is always snug, to the cervix os.

In one embodiment, the annular membrane preferably incorporates one or more, and typically two opposed, cavities at the (preferably thickened) rim of its smaller, central, circular opening, in which cavities are received and retained medical probes such as, for example, an electronic thermal sensor or, more preferably, two ultrasonic transducers. Because the preferable two ultrasonic transducers as are held in complimentary opposed cavities are held pointed towards each other across the cervix os (when the annular membrane is properly inserted), these ultrasonic transducers need not be so omnidirectional as was the case with previous positional affixation of these probes such as by, for example, screwed attachment to the muscle of the cervix os. In other embodiments of the annular membrane, the ultrasonic transducers are simply glued to the membrane, which is substantially planar.

The annular membrane comes in a first embodiment that is similar in form to a female diaphragm in that the membrane (and it supported instrumentation probe(s)) is held in contact with, and about, the cervix os by action of being wedged at the top of the vaginal canal. In another, second, embodiment, the annular membrane is similar in form to a cervical cap, and compressively embraces the cervix os so as to held in position thereupon. Finally, in still another, third, embodiment, the annular membrane is similar in form to a female contraceptive diaphragm, and is lodged in the vaginal canal so high so as to be in contact with the cervix os. In this third embodiment a sheath, or large tube, extends downward from the exterior circumference of an annular ring lodged in the top of the vaginal canal. This tube shields the wire(s) connecting to the probe(s) from the walls of the vagina. Other of the embodiments may also incorporate wire shields of greater or lessor length, sometimes centrally positioned within the vagina so that wires from probes positioned at the cervix os essentially extend straight downwards and out the vagina.

In a variant to any of the embodiments which variant is especially useful if (i) instrumentation probes are to be mounted lower in the vaginal canal, and/or (ii) surgery is to transpire in or through the vaginal canal, the annular membrane may further incorporate within its annulus one or more integral small wire conduits, or channels. Two wires—typically connecting to typically two ultrasonic transducers that are typically mounted at the inner rim of the annulus— are routed to the exterior circumference of the annulus, preferably at the same point, and are then directed downwards into the vaginal canal, by these conduits. If the annular membrane is optionally extended into the vaginal canal, then the conduits, or channels, preferably appear only in that portion of the flexible annular membrane that is mounted at and about the cervix os. This is in order to avoid that any lower-extending small conduit should serve as a pathway for bacteria from the vagina to the region of the cervix.

All these various embodiments and variants with their differing geometries have a purpose: each may be variously useful for positioning and holding one or more probes in some particular position(s) in the vaginal canal, particularly at and across the cervix os, as will later be more fully taught.

The wires and the preferred ultrasonic transducers are coated with a biologically inert material, preferably respectively Teflon® polymeric material Teflon is a registered trademark of E. I. DuPont de Nemours) and EPO-TEK™ coating (epo-tek is a trademark of Epoxy Technology, Inc.). The surgical latex is also biologically inert.

The elastomeric membrane expands and contracts with such cyclical variation in the dilatation and effacement of the cervix os as occurs from the earliest onset of labor until imminent childbirth, and does not interfere with either this natural function nor, if inadvertently not timely removed before delivery, childbirth. In the rare situation that the annular membrane and its retained probe(s) are still within the vaginal canal upon the occurrence of childbirth, the annular membrane and retained probe(s) will be pushed from off its seat on and about the cervix os by the continuing effacement of the cervical wall, and the entire assembly will simply comprise a relatively small and benign item which will be swept, if not earlier pulled, from the birth canal during childbirth.

The annular membrane holding the preferred transducer probes of an ultrasonic cervimeter may safely be situated in place about the cervix os for prolonged periods ranging to a month. Both the annular membrane and its held probe(s) are intended to be (i) entirely disposable, and (ii) changeable by the patient woman herself in the manner of a contraceptive diaphragm or cervical cap. In the rare case the that the medical probe(s) retained by the annular membrane is (are) so expensive that neither disposal nor later reclamation of the used probe is practical, it is relatively straightforward and non-hazardous to (i) extract the membrane and probe(s), (ii) detach the probe(s) from the membrane, (iii) discard the used membrane, (iv) wash and sterilize the probes with a chemical solution, normally alcohol, (v) insert the cleaned probe(s) in a new sterile membrane, and (vi) insert the membrane and its held probe(s) back into position at and about the cervix os. Although the wire end(s) of the probe(s) are preferably plug connected to the biomedical instrumentation, or monitor—and are thus easily unplugged and plugged—it is possible and non-hazardous to do the replacement while the probe(s) is (are) still connected to a still-energized instrument or monitor.

The preferred annular membranes and their held probe(s) are self-aligning and self-centering in position about the cervix os, and a quality replacement may normally be accomplished by an expectant woman herself as well as by her gynecologist or obstetrician. In the event of improper replacement of an annular membrane carrying the preferred ultrasonic transducer probes, the monitor will so indicate by alarming after a period of time that, no or an unreasonable cervical dimension being indicated, the probes are not detectable to be in reasonable and proper positions. Conversely, a good status indication at the cervical dilatation/effacement monitor provides a very high degree of assurance to the woman patient that she has accomplished the replacement satisfactorily. It should be understood that ultrasound cannot be communicated between probe transducers save though such intervening tissue and mucous as is normally found at the cervix os, and that an ultrasonic distance measurement will not transpire between the two ultrasonic transducer probes of a membrane that is merely inserted, for example, into the vaginal canal.

The membrane and its preferred attached ultrasonic transducer probes may alternatively be emplaced only at the onset of labor, and for the purpose of monitoring the progress of labor. The expectant mother need never have previously worn an ultrasonic monitor of cervical dilatation and effacement. The automated electronic cervical dilatation and effacement monitoring is continuous and accurate, and less obtrusive than periodic digital assessment, throughout the progress of labor. Moreover, the latex annular membrane itself is less mentally disconcerting, and likely more familiar in form, to a woman entering labor—who may already somewhat apprehensive—than are the alternative probe affixation means—particularly including corkscrews of considerably daunting appearance.

These and other aspects and attributes of the present invention will become increasingly clear upon reference to the following drawings and accompanying specification.

BRIEF DESCRIPTION OF THE DRAWINGS

FIG. 1 contains a table comparing the advantages and inconveniences of prior art methods of cervimetry with a preferred method, and instrument, used with the annular membrane of the present invention.

FIG. 5a is a graph showing a calibration of the ambulatory cervical effacement/dilatation monitor.

FIG. 5b is a graph showing the typically varying dilatation of the cervix uteri of a human female, or any higher primate, during labor.

DESCRIPTION OF THE PREFERRED EMBODIMENT

Figure 2:
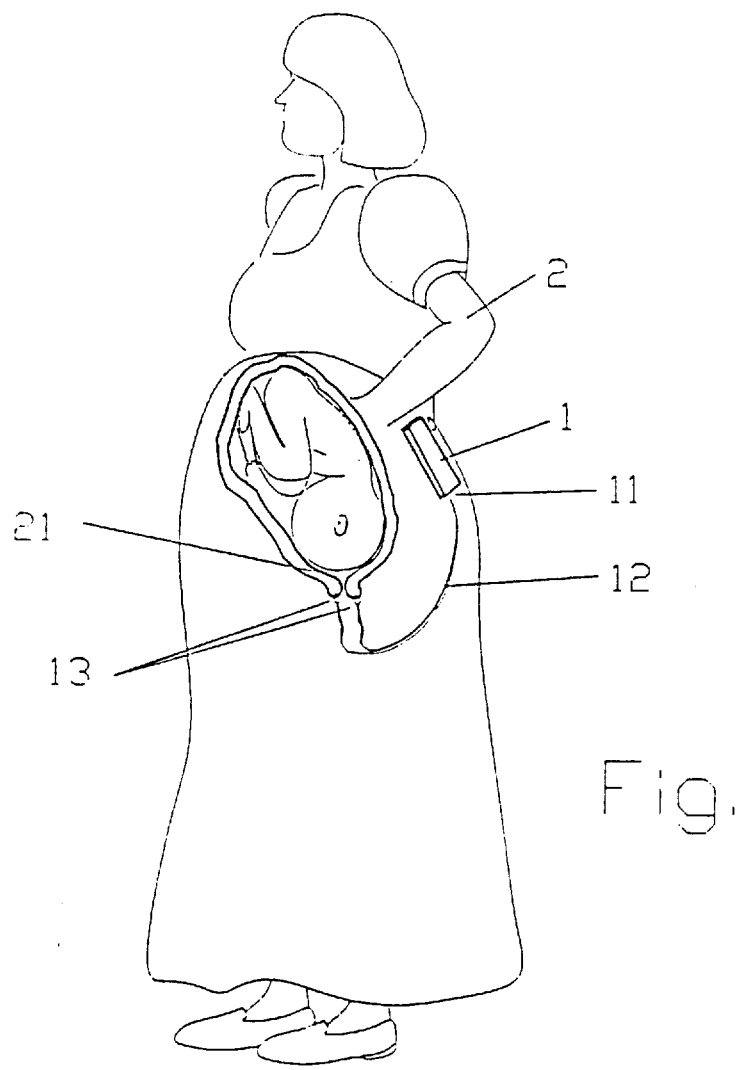
FIG. 2 is a diagrammatic perspective view showing a preferred embodiment of an ambulatory cervical effacement/dilatation monitor having disposable probes in use for monitoring an ambulatory pregnant human female.

The present invention is directed to the holding of medical instrumentation probes at and about the cervix os of a human female. The present invention is particularly directed to holding ultrasonic transducer probes in positions about the cervix os of a pregnant human female for purposes of measuring and of monitoring the dilatation—meaning opening—or, equivalently, the effacement—meaning the thickness of the rim—of the cervix uteri, as attends all stages of labor. It should be noted that as the cervix expands during labor, increasing the dilatation distance, the rim of the cervix stretches and becomes thinner, decreasing the effacement distance, or thickness of the rim. One phenomena is related to the other. Both phenomena show the same cyclical variation during labor, and each may be correlated to the other.

The probes of an ultrasonic acoustic cervimeter with which the holding device of the present invention is beneficially used are preferably affixed across the major chord, or diameter, of the cervix uteri from a one side to the other, or at least across a minor chord for such a maximum distance of separation on the face of the cervix as is possible. In such positions the probes measure dilatation.

However, the probes may be affixed, if required or desired, along but a single radii of the cervix with a one probe located more centrally, on an interior wall of the cervix (which is in the overall shape of a torus) and with the remaining probe located nearby on the exterior wall of the cervix. In such a position the probes measure effacement.

An cervimeter instrument usable with the holding device of the present invention may be implemented in many different forms—ranging from a straightforward ultrasonic acoustic distance measuring device, or sonic cervimeter, to a full-blown computerized cervical dilatation/effacement alarming monitor with a memory and a time-based display of a running history of dilatation/effacement measurements. One preferred embodiment of a cervimeter is as a battery-powered monitor with a memory and a graphical display, plus combined audible and visual alarm indications, that is completely self-contained and portable, and that is intended for continuous use on, partially within, and by, an ambulatory female patient. This embodiment typically takes one hundred (100) measurements a second, forming a running average of the cumulative measurements taken over a period of five (5) seconds and displaying the averaged measurements for the previous one hundred and twenty-eight (128) five-second intervals (for a total of 10⅔ minutes). The cumulative measurements for a longer period are stored to the capacity of memory, typically the averaged measurements for at least the previous six hundred and forty (640) five-second intervals for a total of over sixty (60) minutes. The ambulatory monitor typically so functions on two (2) 9 v.d.c. dry cell batteries, typically for a period of more than eight weeks.

A table comparing the major advantages and inconveniences of prior art methods of cervimetry with such a method, and instrument, of the present invention is shown in FIG. 1. It may immediately be observed that the preferred ultrasonic cervimetry method serves, nonetheless to being performed by an instrument that is uniquely compact and suitable for ambulatory use, to record a history of cervical dilatation/effacement that is described as "total" as opposed to "limited". By this it is meant that previous monitors, especially including ultrasound monitors, recorded a history of cervical dilatation/effacement only when the patient was "hooked up" to the previous monitors, usually in a hospital after the onset of labor. Data regarding any such long or short term transient events during pregnancy as did not lead to the full onset of labor was unrecorded and unavailable. Indeed, very little is known at the present time about exactly what (other than the lapse of time, or intentionally-administered medications) will most likely induce the onset of labor in a particular human female, and what precursors to this event and/or flags to the likely causative agent(s) (such as exercise, or diet, or temperature) might be observed. The cervical monitor for which ultrasonic transducer probes are held in position by the device of the present invention is, of course, dedicated to providing a full and complete record of cervical dilatation/effacement over a period potentially as long as many months. During this period of time there is little or nothing regarding the dilatation (or, equivalently, the effacement) of the cervix that will not be recorded, and archived into a history store that is retrievable to and analyzable by, a health care professional. Accordingly, the recorded history is described as "total".

Because the cervical monitor for which ultrasonic transducer probes are held in position by the device f the present invention is intended to be in continuous use twenty-four hours a day during all periods—which periods may be protracted and many months in duration—when the dilatation (or, equivalently, the effacement) of the cervix of the female patient wearing the monitor is of medical interest, it is possible for the monitor to make a visual or audible alarm when certain conditions are detected. Certain basic conditions regarding the cervical dilatation/effacement curing the onset of, and during the progress of, labor are well understood, and the monitor looks for, and alarms, the occurrence of these conditions.

It may well be, and is expected, however, that certain high-risk pregnancies will exhibit detectable, possibly unique, phenomena prior to events such as spontaneous abortion. If particular warning signs to the continuation of the pregnancy of a particular human female, or class of human females, can be recognized from the study of historical data on such female, or on such class of females, then it is contemplated that it will be desirable to warn such a female or females of the incipient occurrences of such signs in her/their later pregnancies. As will be seen, the ambulatory cervical monitor of the present invention is a programmable device. If necessary or desired, it can be preset to alarm, and to variously alarm, conditionally upon the occurrence of almost any condition(s) of the cervix transpiring over almost any time interval(s) that the monitor is capable of detecting.

Although setting up the ambulatory cervical monitor to alarm upon arbitrarily determined criteria (one, or many) involves (as of the present degree of understanding of cervical dilatation/effacement indications in high-risk pregnancies) highly skilled labor and attendant expense, it should be understood that the monitor is intended to be used, among other applications, on pregnant females that have never successfully carried so long so as to give live birth, let alone to term. Moreover, it should be understood that if cautions performed by the female and/or her medical advisors in response to monitor alarms and/or recorded records can prevent, or can even slightly delay by a matter of months or even scant weeks, highly premature births, then the very considerable expense of administering to premature newborns can be ameliorated, or even substantially saved.

This simple concept deserves further exposition. People do not like to, and effectively cannot, be told that they cannot have children because they are at risk of giving birth prematurely, and at great expense. People, especially those who desire but do not yet have children, do not like to think that such medical care, no matter how expensive, as might permit their prematurely born child to survive is being withheld on economic grounds. An ounce of prevention is worth a pound of cure—although it is perhaps not so "showy" in terms of hospital obstetrics facility, practice, and practitioners. A successful obstetrician in the current U.S. health care environment (circa 1994) is one who judiciously avoids problems, not just one who is skilled in overcoming problems. The cervical monitor with which the probe holder of the present invention is preferably used is directed to aiding an obstetrician, a general health care practitioner, and a woman patient herself, in avoiding the expense, risk, and potentially traumatic consequences of premature birth.

A diagrammatic perspective view of a preferred embodiment of an ambulatory cervical effacement/dilatation monitor 1 having disposable probes 13 in use for monitoring a pregnant human female 2 (shown partially in cut-away view and partially in phantom line) is shown in FIG. 2. The female 2 is ambulatory. Wires 12 connect a portable control unit 11 to the probes 13, The wires 12 descend (in the standing female) from the cervix os 21 whereat the probes 13 are affixed through the vagina (not shown) to the exterior of the body of the female 2. They then proceed past normal boundaries and apertures of both underclothing and clothing to the site of the control unit 11, which may be worn virtually anywhere on the body in a position covered or uncovered by clothing as is desired. The wires 12 are normally quite small and flexible, and are appropriately sheathed in soft and flexible plastic. The preferred surrounding plastic is preferably (i) surgical grade, (ii) antibacterial, (iii) and readily cleansed. The wires and probe bodies are preferably coated with epo-tek™ coating available from Epoxy Technology, Inc., 14 Fortuna Drive, Dillerica, Mass. 01821 U.S.A. (epo-tek is a trademark of Epoxy Technology, Inc.).

The entire interconnection system of the wires 12 is designed with due consideration to (i) comfort for long term wear, and (ii) avoidance of establishing any path by which germs might abnormally be conducted to the region of surface of the cervix 21.

Figure 3A:
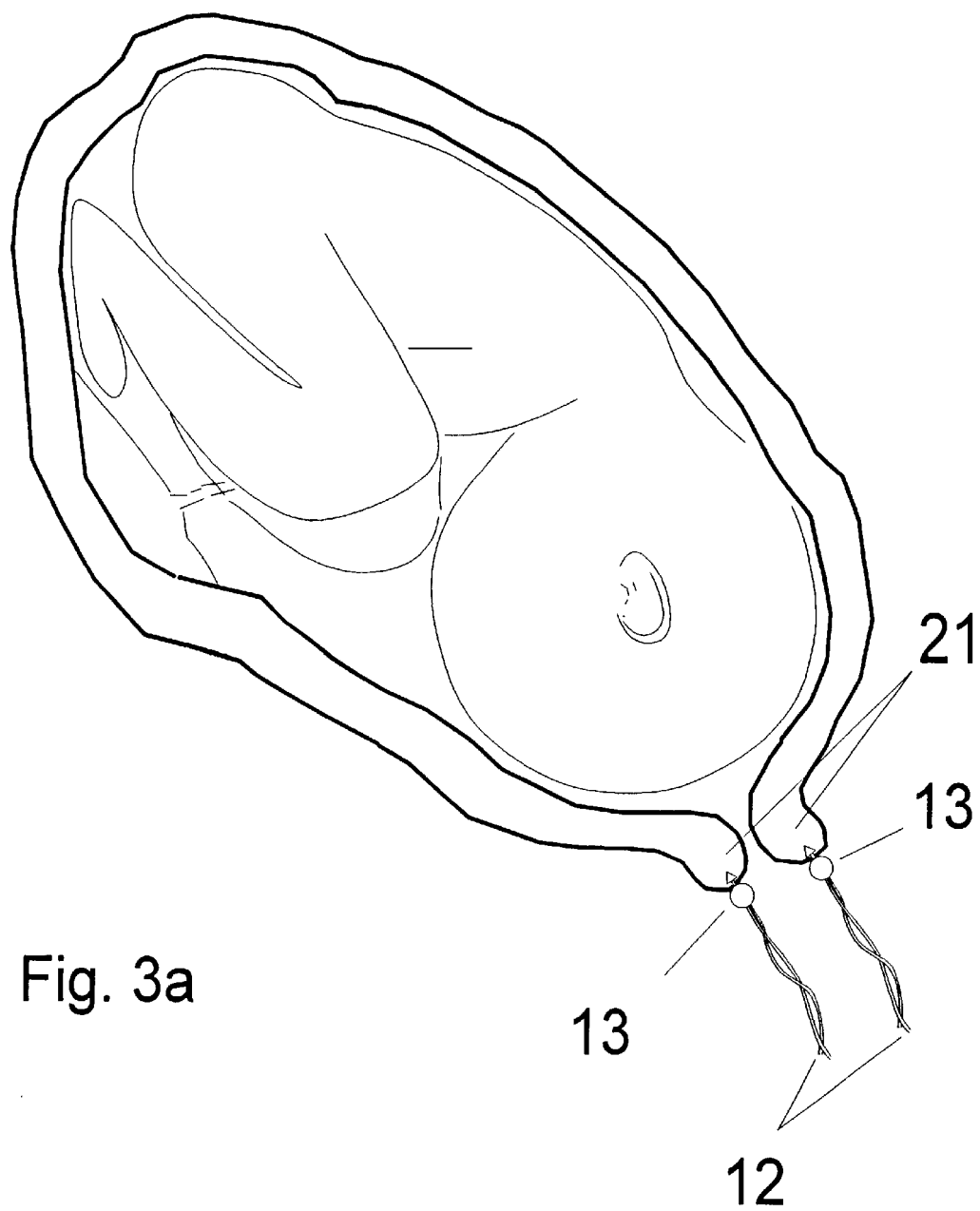
FIG. 3a is a detail diagram of first positions of affixation of the disposable probes of the ambulatory cervical effacement/dilatation monitor to the cervix uteri of the ambulatory pregnant human female previously seen in FIG. 2, the first affixation positions being so as to monitor cervical dilatation.

A detail diagram of the affixation of the disposable probes 13 of the ambulatory cervical effacement/dilatation monitor 1 to the cervix uteri 21 of the pregnant human female 2 (previously seen in FIG. 1) is shown in FIG. 3. The particular affixation of the probes 13 that is illustrated is where each of the two probes is on the rim of the cervix 21 at roughly 180° separation. In this position the probes 13 are positioned to measure, by the delay in an ultrasound pulse traveling between them, the cervical dilatation, or distance across the cervix. Note that in the FIG. 3 it appears as if the central opening of the cervix os is void and filled with air, which would be unsuitable to transmit ultrasound. In actual fact the complete path in a substantially straight line between probes 13 is completely filled with tissues, mucous and fluids. An ultrasonic path can be reliably established and maintained between the probes 13 under all normal and abnormal conditions. Indeed, neither ultrasonic signal attenuation nor change in attenuation (signal level) presents any significant problem(s) or challenge(s)—at least when the preferred probes are used (as will be discussed in conjunction with FIG. 4)—and there is little difficulty that (i) and ultrasonic pulse emitted at a one of the probes 13 will be duly received and the other one of the probes 13, and that (ii) this pulse will travel a true path, meaning straight between the two probes 13.

Figure 3B:
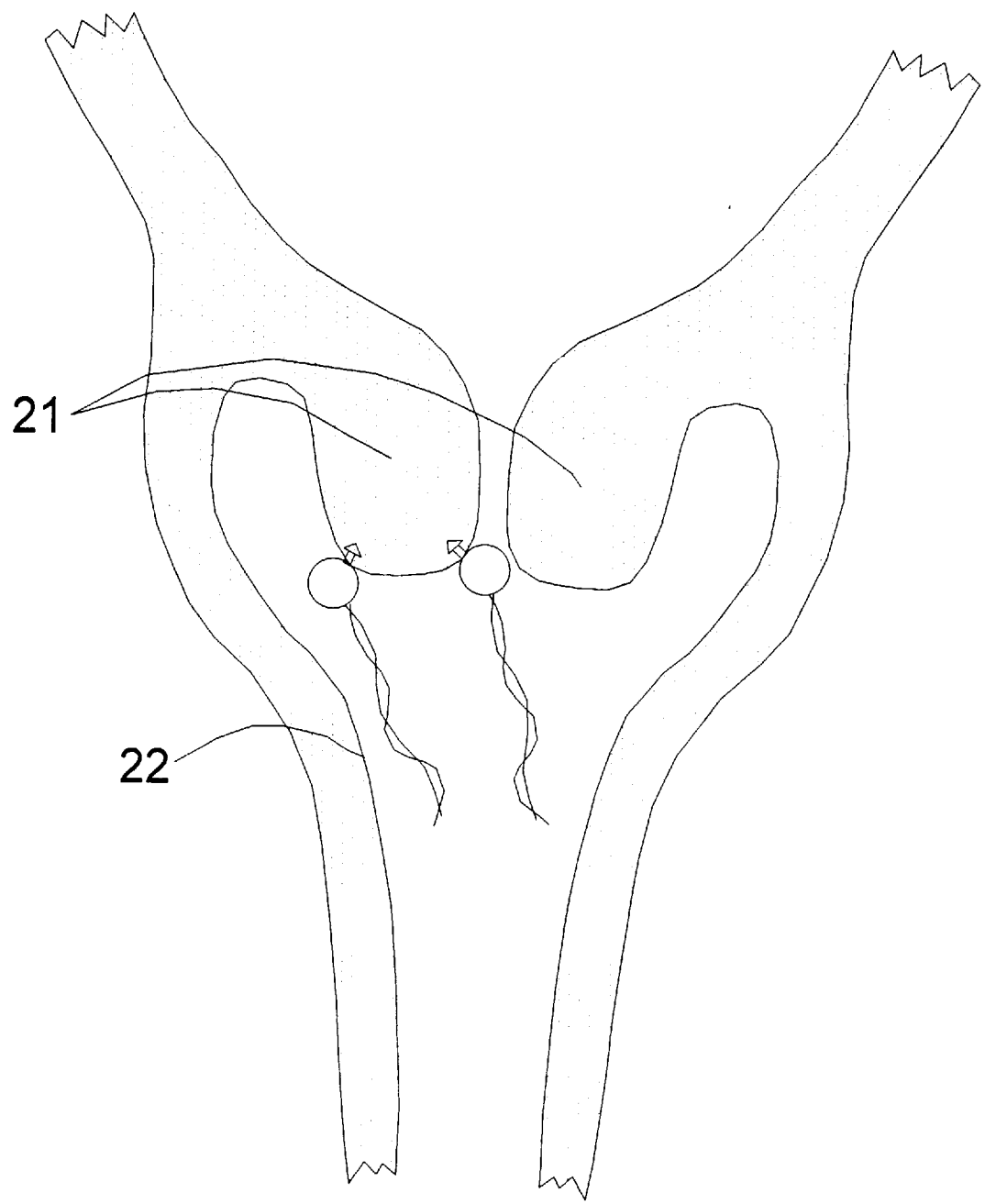
FIG. 3b is diagram, at an enlarged scale from FIG. 3b, of a second positions of affixation of the disposable probes to the cervix uteri of the pregnant human female previously seen in FIG. 2, the second affixation positions being so as to monitor cervical effacement.

A diagram, at an enlarged scale from FIG. 3b, of one mode of affixation of disposable probes to the cervix uteri of the pregnant human female in positions to monitor effacement is shown in FIG. 3b. The probes 13 are mounted along a same wall region, and normally on opposite sides of the wall, of the cervix os 21. When the cervix os 21 dilates (enlarges) then the distance between the probes 13 as such are attached in FIG. 3a will increase. However, during the same dilatation (enlargement) the distance between the probes 13 as such are attached in FIG. 3b will decrease. The increase is related (although not linearly) to the decrease, and vice versa. The status of the cervix os may be monitored, and interpreted, from data concerning either dilatation or effacement (or both). The normally measured, observed, monitored and interpreted quantity is dilatation, and the ensuing discussion of the function of the cervical monitor of the present invention will be based on dilatation. However, a practitioner of the medical arts will understand that these and other physiological measurements are interrelated, and that the monitoring and alarming function of the present invention is not dependent upon the particular placement of the probes 13, nor the particular path and distance that is monitored.

Figure 4C:
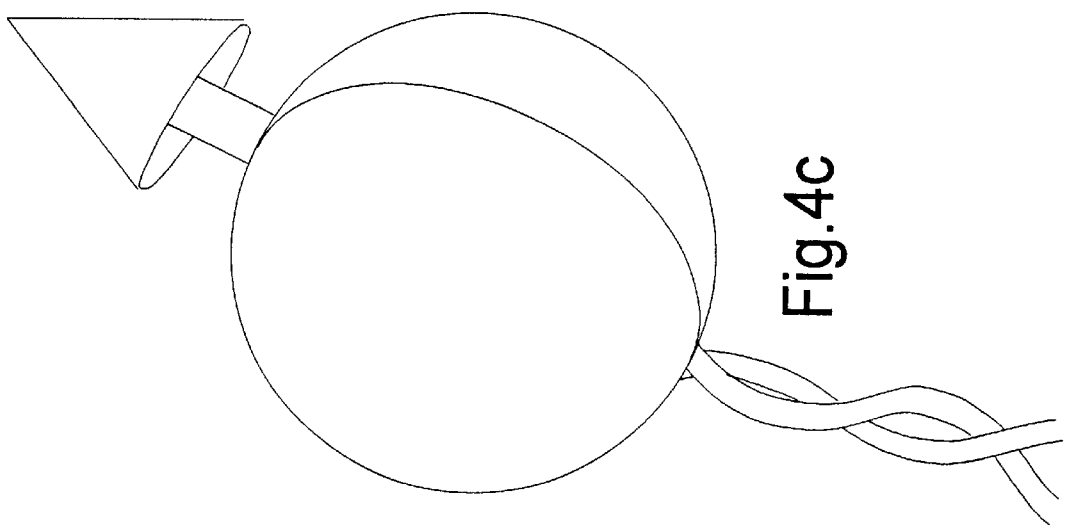
FIG. 4a through Figure show various preferred embodiments of the heads of disposable probes, two of which probes which are used with the preferred embodiment of the ambulatory cervical effacement/dilatation monitor previously seen in FIGS. 2 and 3.
FIG. 4d shows a cross-sectional view of the construction of a preferred spherical transducer previously illustrated in FIG. 4c.
FIG. 4e is a detail view of this same transducer as assembled.
Figure 4B:
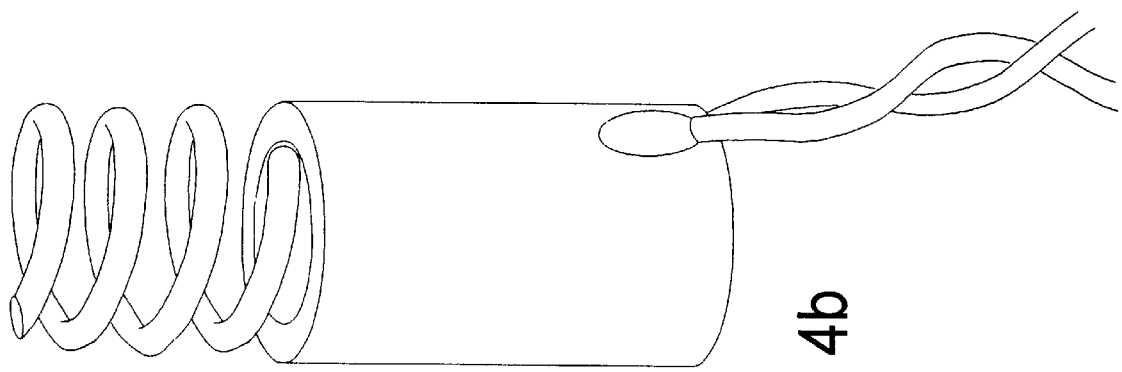
Figure 4A:
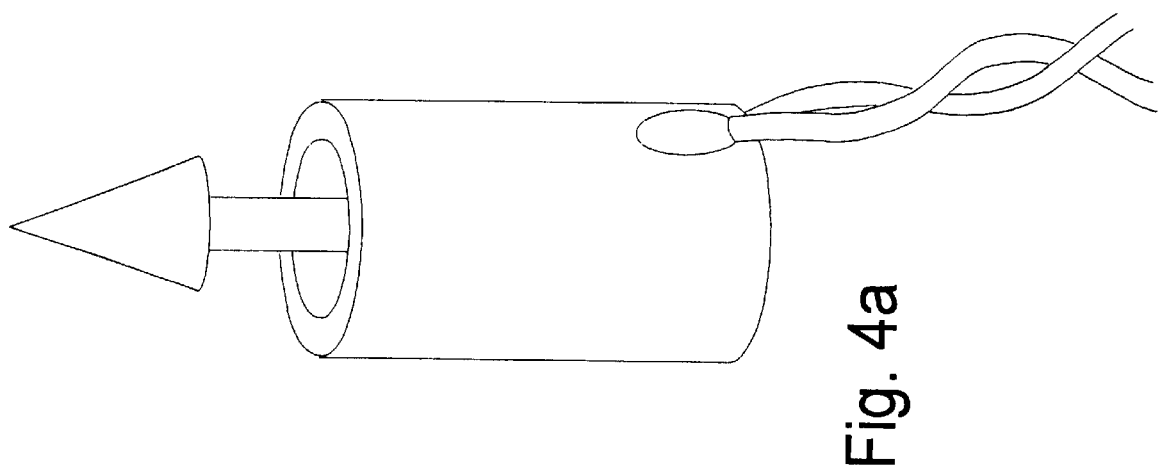

Various preferred embodiments of the head of a disposable probes, two of probes which are used with the preferred embodiment of the ambulatory cervical effacement/dilatation monitor previously seen in FIGS. 2 and 3, are shown in FIG. 4, consisting of FIG. 4a through FIG. 4c. The body of the embodiments of FIGS. 4a and 4b is substantially cylindrical whereas the embodiment of FIGS. 4c is substantially spherical. The transducer of each of these two body configurations is in the substantial shapes of a three-dimensional, non-planar, bodies. This is somewhat unusual because an ultrasonic transducer is normally housed in a substantially planar parallelepiped body, typically a disk. Such need not be the case, however. The ultrasound, which is electrically produced in a crystal, will radiate from the surface of the surrounding housing, whatsoever its shape.

Each of the preferred transducer bodies shown in FIGS. 4a–4c is characterized in that ultrasound emissions from the transducer occur along a multiplicity of axis in multiple different directions. The reason that the transducers are so omnidirectional is that, when secured to the wall of the cervix uteri of human female such as by a barbed fishhook or corkscrew coil (to be discussed), the transducers are substantially insensitive to their initial placement(s) and alignment(s), and also to any directional changes occurring before or during labor. The preferred transducers serve to maintain good acoustic coupling under all conditions.

Figure 4D:
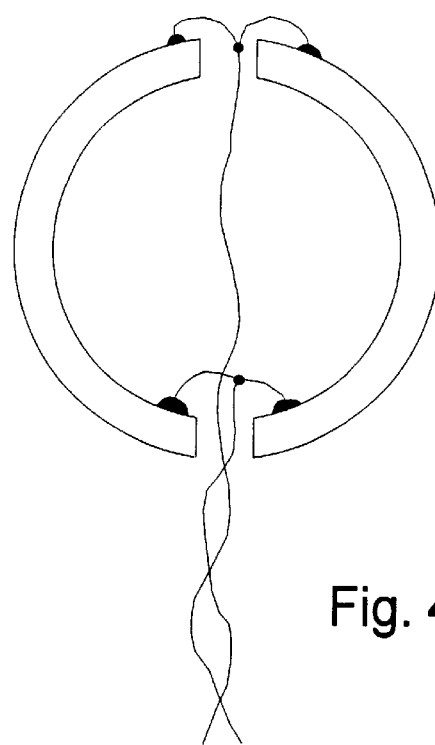
Figure 4E:
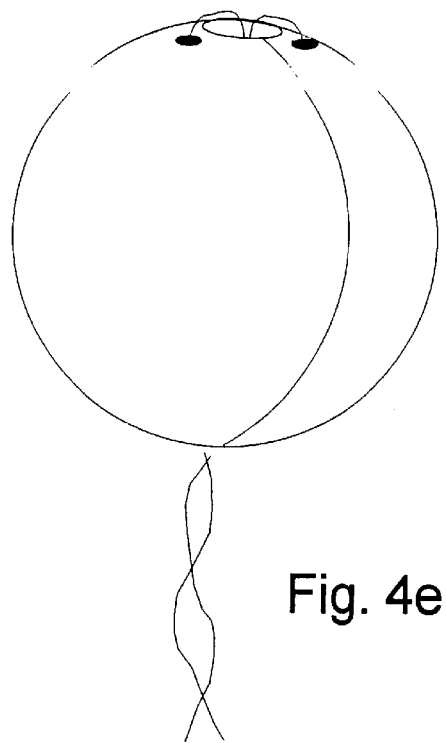

The particular construction of the preferred spherical transducer previously illustrated in FIG. 4c is shown in cross-sectional view in FIG. 4d. A detail perspective view of this same transducer as assembled is shown in FIG. 4e. The preferred spherical transducer is formed from the union of two ceramic hemispheres coated on the interior and the exterior with metal. Each hemisphere is a polarized piezo-electric. Wired connections are as shown. The device is available from Channel Industries, Santa Barbara, Calif., U.S.A.

It is, or course, necessary to maintain the transducers 13 in their predetermined, fixed, locations upon the cervix os 21 so that ultrasonic transit time measurements may be performed. That is the purpose of the holding device of the present invention. However, it should be preliminarily understood that no such separate holding device, per se, is absolutely necessary. There are insubstantial nerve endings on the cervix os, which is also physically very robust and resilient to permanent damage. Ultrasonic probes have heretofore been attached by corkscrews, and that embodiment of a probe 13 that is shown in FIG. 4b continues this tradition. Corkscrews are a good, and proven, means of attachment of probes to muscle, as witness cardiac pacemakers. However, there are differences between cardiac probes and ultrasonic transducers. In the former case an electrical signal is being coupled to the muscle, and reliable continuous electrical and physical contact must be maintained therewith. In the present ultrasonic probes, understand that no electrical, nor acoustical, energy is being attempted to be coupled into the muscle (of the cervix os) through, or by, the probe attachment. There is, or course, no electrical coupling to the muscle. The acoustic coupling is, by and large, to the surrounding mucous and fluids, and the probe is not configured for coupling acoustic energy into the cervix os (if it was then should lie tight against the cervix os). The probes' attachments are simply to hold the probes in position so that they may follow the movement of the muscle, and so that the varying distance between them may be monitored.

So considering the function of the attachment of a probe 13, the barbs of the embodiments of FIGS. 4a and 4c, of like barbs in the substantial shapes of fishhooks, are preferred for some patients. Namely, the barbed probes are generally easier, and faster, to attach in patients who are sensitive to discomfort. A corkscrew probe should be unscrewed in order to remove, but a barbed probe of the design of FIGS. 4a and 4c will usually exit cleanly if simply pulled strongly. In those generally rare affixations, and locations, where a fishhook barb (not shown) better serves retention, and positioning of the probe, then the barb may be removed exactly as a fishhook is removed from the flesh of the body. Namely, the barb is worked forward to exit the surface, and is cut off as exposed. The barb-less probe is then withdrawn.

Despite the fact that the performance of these methods and structures for probe affixation is unquestionably effective, there is a very great psychological problem in explaining to a woman that devices that look so "vicious" and so potentially injurious as do the barbed and corkscrew probes are to be affixed within in her body, and at a location thereof that she typically (wrongly) regards as sensitive. Furthermore, the barbed and corkscrew probes must be both inserted and extracted by the woman's obstetrician or other health care professional, and are not suitable for selfinsertion or extraction. For these reasons, the alternative probe emplacement and holding system of the present invention will be shown commencing with FIG. 9.

In the meanwhile, a graph showing a calibration of the preferred ambulatory cervical effacement/dilatation monitor is shown in FIG. 5a. The calibration is performed in the controller 11 by producing in manually controllable steps successive delays such as would be indicative, if received from probes 13, of an increasing amount of separation between the probes 13. The "manually controllable steps" simply involve the stepwise rotation of a multiple position switch which, in its successive positions, couples an increasing amount of delay into the simulated probe input to the controller 11 (the schematic diagram of which controller 11 will be shown in FIGS. 6 and 7). The lowest level of the trace in the graph of FIG. 5a is indicative of a probe separation of 10 mm; the highest level of the trace is indicative of a probe separation of 60 mm. If the number of steps are carefully counted, if may be observed that the preferred resolution of the cervimeter monitor 1 is at least as small as 5 mm.

FIG. 5b is a graph showing the typical varying dilatation of the cervix uteri of a human female, or other higher primate such as a rhesus monkey, during labor. The total period shown is about thirty (30) minutes in which period twenty (20) relatively even cycles have transpired for an average cycle time of one and one-half (1½) minutes per cycle.

Figure 6:
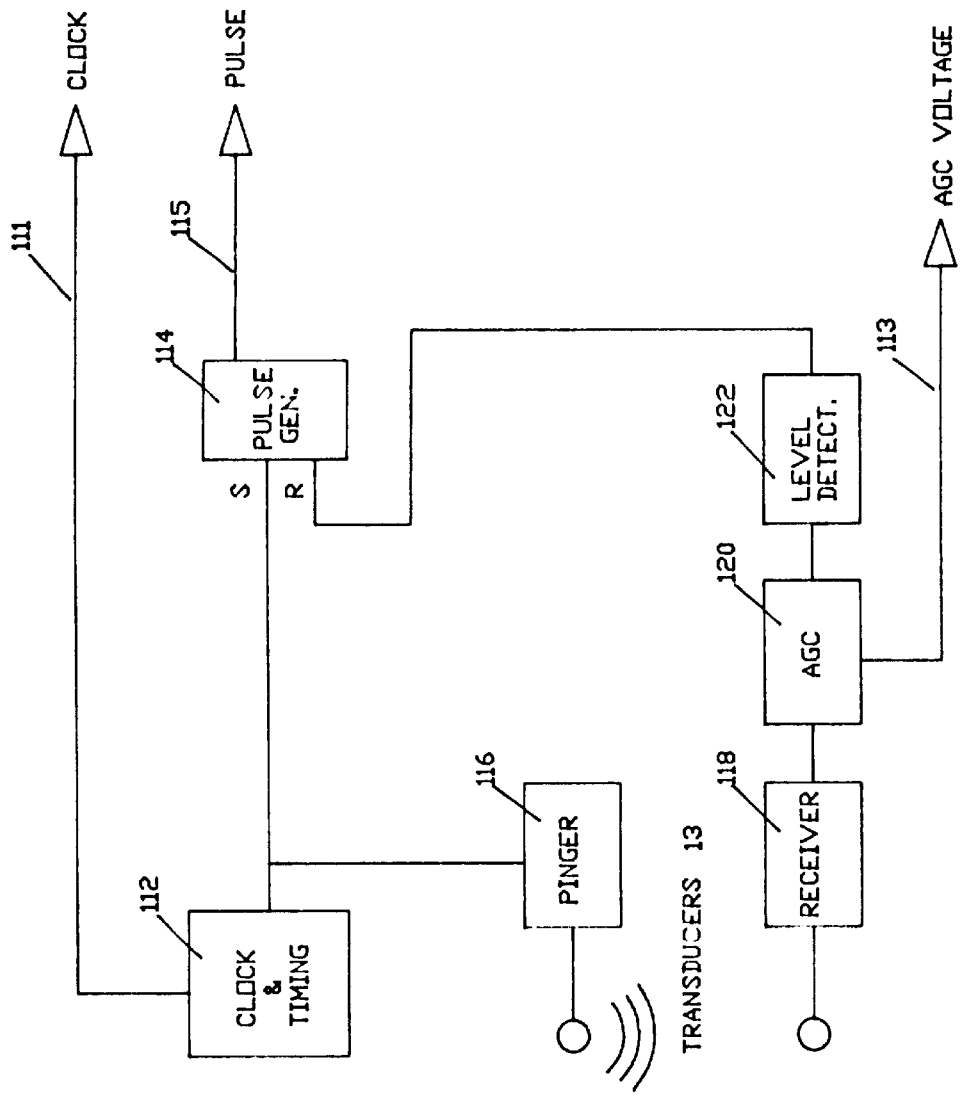
FIG. 6 is a schematic block diagram of a substantially analog first portion of the preferred embodiment of the ambulatory cervical effacement/dilatation monitor previously seen in FIG. 2.

A schematic block diagram of a substantially analog first portion 11 of the preferred embodiment of the ambulatory cervical effacement/dilatation monitor 1 in accordance with the present invention is shown in FIG. 6. The first portion 11 is, in of itself, a complete sonomicrometer. Sonomicrometers are known in the art, and the circuit of the block diagram of FIG. 6 is simply a particular version of a sonomicrometer that is, quite obviously, adapted to the measurement task at hand in terms of (i) acoustic signal power, (ii) acoustic signal reception sensitivity, and, most importantly, (iii) the duration (not the frequency) of an acoustic signal pulse that will be appropriate to measure the distances involved in cervical dilatation, and (iv) a repetition rate of the acoustic signal pulse that will be appropriate to measure all changes in the distances involved in cervical dilatation. Notably, the frequency of the acoustic signal is an innate property of the probes, or transducers 13, which "ring" when electrically excited at their resonant frequency(ies). The probes, or transducers, 13 may suitably operate over a broad range of ultrasonic frequencies, and preferably ring at a natural resonant frequency of about 5 Mhz.

A CLOCK portion of the CLOCK AND TIMING 111 produces a fundamental 1.58 MHz frequency. This frequency is chosen because an ultrasonic acoustic pulse will travel approximately 1 millimeter in tissue—and very nearly the same in mucous or other water-based fluids—in the period of one cycle of 1.58 MHz, or 0.63 microseconds. The 1.58 Mhz signal is provided as signal CLOCK 111.

A TIMING portion of the CLOCK AND TIMING 112 produces pulses of (i) 50 microsecond duration (of 1.58 MHz signal) (ii) at a pulse repetition rate of 100 Hz. The duty cycle of the collective pulses is correspondingly (($5 \times 10^{-5}$)$\times 1 \times 10^2$) per second, or a low 0.5% which serves to save power. These 50 microsecond pulses at the 100 Hz. rate are applied to the set, or S, input of the PULSE GENERATOR 116 and the PINGER 114. The PINGER 116 serves as an amplifier. The 50 microsecond pulse duration is sufficient, when driven by the PINGER 114, so as to cause the driven one of the probes, or transducers, 13 to ring, producing an acoustic pulse (which gradually decays in amplitude) for an effective duration, as is such pulse is detectable at the other one of the transducers 13 and by the RECEIVER 118, of about 1 msec. (One hundred such acoustic pulses each second give an acoustic duty cycle of approximately 10%.) The duration of this acoustic pulse is, or course, not particularly important save that each pulse shall have completely died away before a next later pulse is generated. In accordance with the principles of transit time sonomicrometry, it is the delay incurred by this pulse in reaching the receiving one of the probes, or transducers, 13 that is important. Each and every pulse will incur a delay of about 0.63 microseconds per millimeter traversed.

The signal developed in the RECEIVER 118 in response to each received acoustic pulse is shaped in an automatic gain control, AGC, circuit 120 and is then subject to detection in LEVEL DETECT circuit 122. The signal AGC VOLTAGE 113 is a function of the amount of signal gain being applied in, and by, the AGC circuit 120, and will be highest when the received signal acoustic is lowest, or non-existent (as between acoustic pulses, or before an acoustic pulse has arrived). A use of such signal AGC VOLTAGE 113 will be later shown in FIG. 7. The signal output of LEVEL DETECT circuit 122 will assume a logic High condition within a few tens of nanoseconds that the acoustic pulse is received by the RECEIVER 118. The signal will, as applied to the reset, or R, input of the PULSE GENerator circuit 114, serve to reset this circuit. (It will be understood that electrical delays are small in relation to acoustic delays in a sonomicrometer.) The signal PULSE 115 arising from the PULSE GENerator circuit 114 accordingly starts with each transmission of an acoustic pulse, and ends with the reception of the same pulse. Its duration is thus indicative of the acoustic delay in the communication of the ultrasonic pulse between the two transducers 13.

Figure 7:
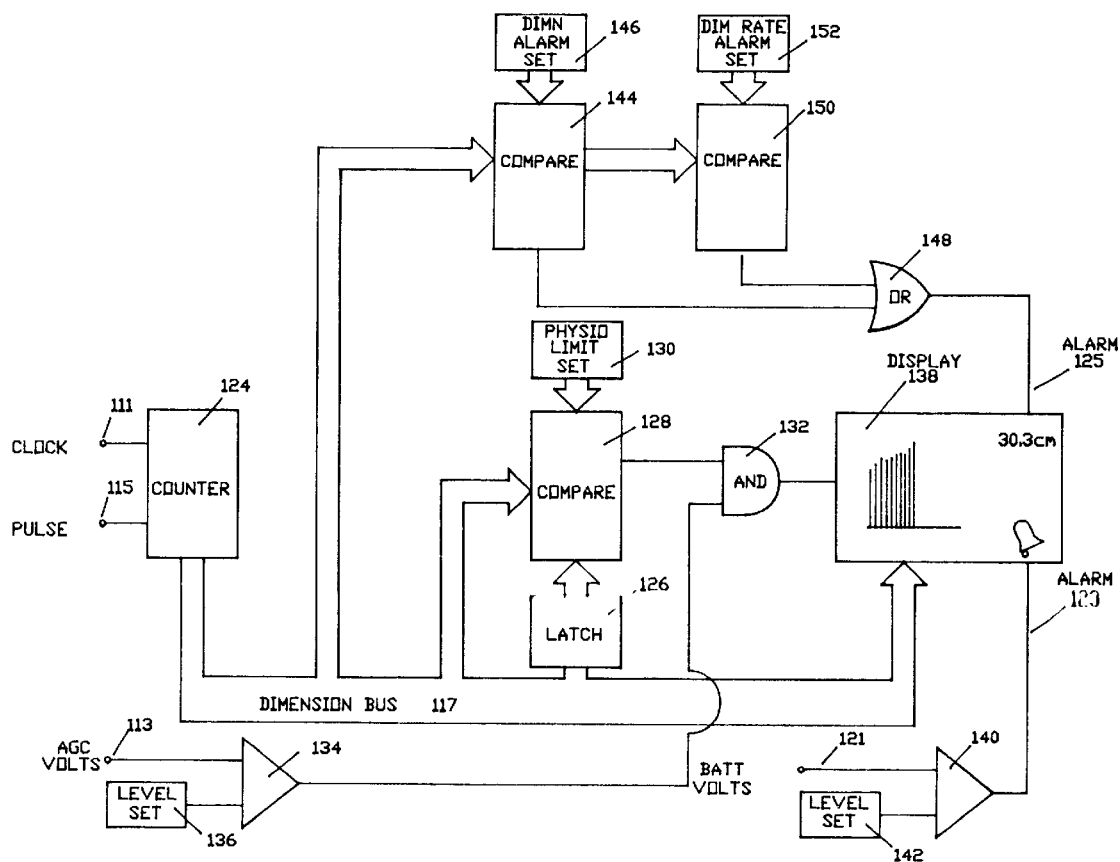
FIG. 7 is a schematic block diagram of a substantially digital second portion of the preferred embodiment of the ambulatory cervical effacement/dilatation monitor, the analog portion of which ambulatory cervical effacement/dilatation monitor was previously seen in FIG. 6.

FIG. 7 is a schematic block diagram of a substantially digital second, data logger and alarming, portion of the preferred embodiment of the ambulatory cervical effacement/dilatation monitor 1. This data logger and alarming portion receives all three signals 111, 113, and 115 developed in the analog, sonomicrometer, portion previously seen in FIG. 6. The signal CLOCK, which is at a frequency of 1.58 Mhz, serves to increment a COUNTER 124 that is enabled for counting for the duration of signal PULSE 115. The number of counts accrued during the duration of each signal PULSE 115 is the thus the distance in millimeters that the ultrasonic acoustic signal traversed between probes 13 (shown in FIG. 6). Permitting the COUNTER 124 to read directly in millimeters avoids the necessity of a later conversion. Once the count is terminated by the logic Low condition of signal PULSE 115, the COUNTER 124 will put the accrued count onto a digital communications bus that is called DIMENSION BUS 117 because it carries the cervical dimension. The COUNTER 124 will also reset itself to zero for the next counting interval (which, in accordance with CLOCK AND TIMING 112 shown in FIG. 6, will occur in 10 milliseconds).

The current count, which is the cervical dilatation (or effacement) in millimeters, is received into a LATCH 126 and a COMPARE circuit 128. The COMPARE circuit 128 also receives a digital quantity from the PHYSIO LIMIT SET register 130. This quantity represents the greatest reasonable, real-world, change that would be expected in cervical dilatation over the time interval between successive counts, or 10 milliseconds. This quantity is equivalent to a change in cervical diameter of about 1 millimeter per second. The previous cervical measurement that was stored in LATCH 126 is compared with the current cervical measurement received via DIMENSION BUS 117, and with the maximum expected change received from PHYSIO LIMIT SET register 130 in order to make the single determination that the presently-received cervical dimension either is, or is not, reasonable. An unreasonable reading might be received, for example, due to ultrasonic noise. If the cervical dimension, as is upon the DIMENSION BUS 117, is reasonable then the input from the COMPARE circuit 128 to the AND gate 132 is a logic High, satisfying one of the two inputs to AND gate 132.

The other, remaining, input to the AND gate 132 is derived from differential amplifier 134. The signal 119 from this differential amplifier 134 will be a logic High, satisfying the remaining one of the inputs to AND gate 132, at such times as the signal AGC VOLTAGE 113 is greater than a preset signal level supplied from the reference voltage level, or LEVEL SET 136. The signal AGC VOLTAGE 113 will so be greater than the preset signal level supplied from reference voltage level SET 136 when, and upon such times, as the RECEIVER 118 (shown in FIG. 6) is not receiving an ultrasonic pulse. According to being in an interval between the reception of ultrasound, the COUNTER 124 is not incrementing, and the cervical dimension that is upon the DIMENSION BUS 117 driven from the COUNTER 124 is (momentarily) stable, and invariant. Satisfaction of the AND gate 132 will produce a logic High gating signal to the DISPLAY 138, and will cause the DISPLAY 138 to capture the cervical dimension quantity that is upon the DIMENSION BUS 117 and to display it as a vertical bar in a next successive position proceeding towards the right across a visual display area.

The display 138, if not substantially the entire data logger shown in FIG. 7, may optionally, and even preferably, based upon a microprocessor. A practitioner of the digital logic design arts will have no difficulty in accomplishing the counting and comparison functions already discussed in FIG. 7, as well as certain other functions to be discussed, in the logic and the registers of a microprogrammed microprocessor. A microprocessor may, for example, scale the cervical dimension received on DIMENSION BUS 117 in order to appropriately size, and place, a graphical display on the DISPLAY 138. Indeed, almost as soon as the practitioner of the digital logic design arts starts to think about the flexibility, and power, of a microprocessor as applied to the data logging and alarming task of FIG. 7, it is possible to realize that, other than the necessity of comparing analog signal levels in the differential amplifier 134 (and also in differential amplifier 140, yet to be discussed) and displaying data in the DISPLAY 138, veritably everything could be done in a microprocessor. In such a case FIG. 7 could be equally validly considered as a functional, as opposed to a hardware, block diagram.

The preferred implementation of the monitor is, as is shown in FIG. 7, to (i) use a microprocessor (not shown) as part of DISPLAY 138, but (ii) not to place have all such functionality as might conceivably be accomplished by the microprocessor so accomplished. This is for two reasons not immediately apparent on the face of FIG. 7. First, it is contemplated that, with an appropriate data storage memory and sequential memory addressing (not shown) that a power-consuming microprocessor and a visual display might be turned off for periods of time and from time to time, saving energy when no one cares to view historical cervical dilatation (effacement) data in the DISPLAY 138. Second, and although various alarms the development of which is yet to be discussed are shown to be communicated directly to the DISPLAY 138, and presumably to any microprocessor (not shown) lodged therein, if is very simple to understand that, by use of discrete circuits no more complex than a latch, it would be possible to register, and to sound and/or display (in the form of a light, or LED), one or more alarms without the involvement of any microprocessor, or microcode program. Although outside the scope of the present disclosure, the data logging and alarming circuitry of FIG. 7 can thus readily be made to have (i) a reduced-power, fullback, operational mode, and/or (ii) substantially fail-safe operation.

An alarming monitor of cervical dilatation/effacement does not incur the reliability requirements of, for example, a cardiac pacemaker. If the instrument fails the patient neither aborts, nor gives birth, nor suffers any adverse effects whatsoever. However, it is anticipated that, in some pregnancies, successful live birth may be dependent upon the adequacy and continuity of the cervical monitoring, and the timely administration of all such interventions (primarily drugs) as are indicated to be prudent and necessary as a result of such monitoring. Accordingly, the cervical dilatation (or effacement) monitor is desirably, and is, constructed as a quality instrument, with due regard by design for its potentially crucial function.

Continuing in FIG. 7, a battery (not shown), nominally of a 9 v.d.c. type which typically suffices to last at least two (2) weeks and more commonly two (2) months in continuous use, produces a battery voltage BATT VOLTS 121. This battery voltage is compared in differential amplifier 140 to the voltage output of a constant voltage circuit LEVEL SET 142. Until, an unless, the battery voltage falls below a predetermined level, normally eight (8) v.d.c., the signal ALARM 123 will be maintained a logic High level, and the DISPLAY 138 will not produce an alarm. At any such times as the battery voltage were to fall below the predetermined level the signal ALARM 123 will go to a Logic Low level, and the DISPLAY 138 will produce a visual and/or audible alarm in plenty of time to replace the battery (not shown) before power reserves are exhausted.

A comparison of the cervical dilatation (effacement) measurement as is present on the DIMENSION BUS 117 is made in, and by, COMPARE circuit 144 to a predetermined dimension that is stored in the DIMN ALARM SET register 146. The DIMN ALARM SET register 146 is intended to contain a maximum dimension in the case of evaluating cervical dilatation, or, conversely, a minimum dimension in the case of evaluating cervical effacement, which, when the cervical dimension is respectively greater than or less than the stored dimension, is indicative that labor has begun (or at least of an extreme cervical condition). The result of the comparison is communicated to OR gate 148 as a logic High signal in the event that the threshold is exceeded. The predetermined dimension that is stored in the DIMN ALARM SET register 146 is preferably adjustably so predetermined, and stored. A microprocessor (not shown, typically closely associated with DISPLAY 138) may facilitate this storage, normally of a value that is determined by the attending physician or obstetrician.

In a similar manner, another comparison of the cervical dilatation (effacement) measurement made in, and by, COMPARE circuit 152 to a predetermined dimension that is stored in the DIMN RATE ALARM SET register 152. Notably, the cervical dimension is not even transferred to the COMPARE circuit 152 until the COMPARE circuit 144 is satisfied, meaning that a threshold cervical dilatation/effacement measurement has been exceeded. The DIMN RATE ALARM SET register 152 is intended to contain a minimum rate of the change of dimension cervical dilatation, or effacement. This quantity is involved once labor has begun (which was presumptively determined by satisfaction of COMPARE Circuit 144). If the predetermined rate of change is not exceeded then this may be indicative of problems with the progress of labor. The result of the comparison is also communicated to OR gate 148 as a logic High signal in the event that the predetermined rate of change is not exceeded. The predetermined rate of change that is stored in the DIMN RATE ALARM SET register 152 is preferably adjustably so predetermined, and stored. A microprocessor (not shown, typically closely associated with DISPLAY 138) again facilitates this storage, normally again of a value that is determined by the attending physician or obstetrician.

Satisfaction of the OR gate 148 produces a logic High signal ALARM 125, which signals received into DISPLAY 125 is used to produce a visual and/or audio alarm.

Figure 8:
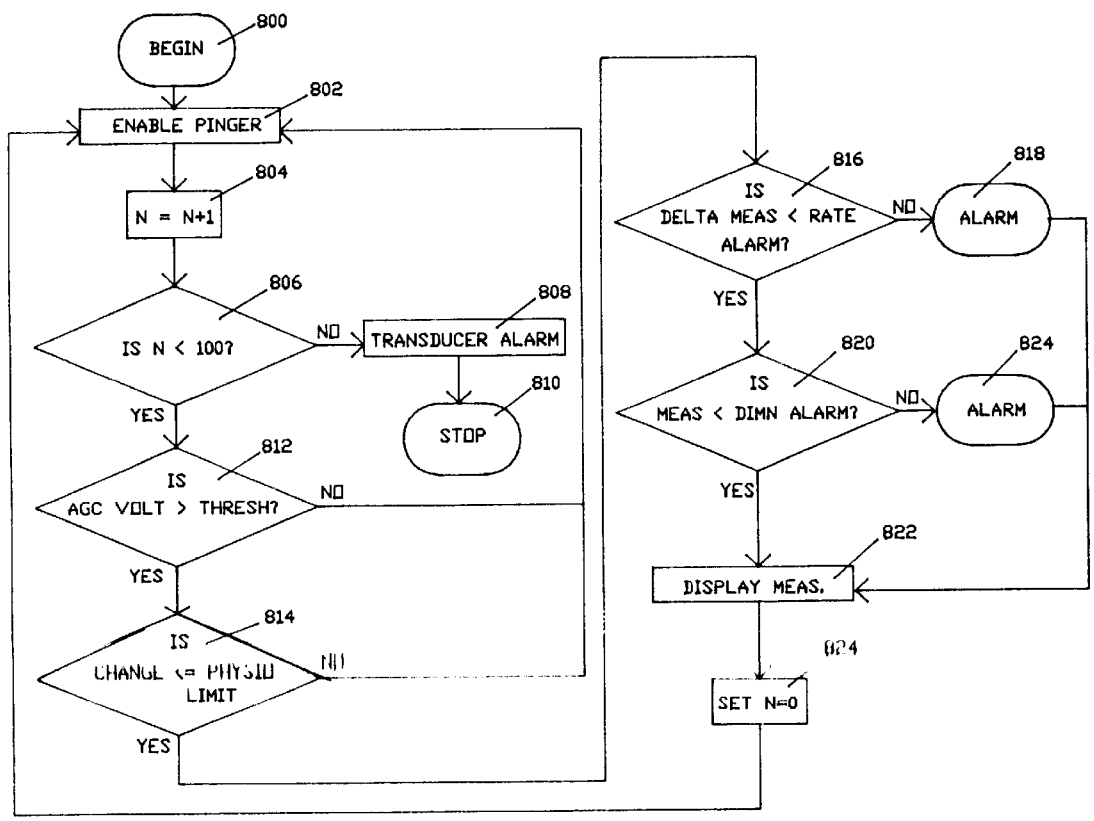
FIG. 8 is a flow chart of the function of the preferred embodiment of the ambulatory cervical effacement/dilatation monitor previously seen in perspective view in FIG. 2, and in schematic block diagram in FIGS. 6 and 7.

A flow chart of the function of the preferred embodiment of the ambulatory cervical effacement/dilatation monitor 1 is shown in FIG. 8. The flow chart is, as well as being functional, suitable to serve as the flow chart of a sequential controller, particularly (but not necessarily) including a microprogrammed microprocessor. It will be recognized by a practitioner of the digital circuit design arts that the relative simplicity of the functional control block diagrammed in FIG. 8 may be accomplished by, and in, many alternative circuit implementations including, but not limited to, a microprogrammed microprocessor circuit.

The function of the ambulatory cervical effacement/dilatation monitor 1 commences with BEGIN block 800 upon application of power, and proceeds to commencing ultrasound transmission with ENABLE PINGER block 802. An ultrasound, or "ping", transmission count N is incremented in block 804, and inquiry is made as to whether this count has exceeded 100 in block 806. As will be developed in the further explanation of FIG. 8, it is a highly abnormal condition, indicating that at least 101 ultrasound pulses have been transmitted with no intervening receptions, if N is greater than 100. In such an eventuality, transducer or transducer interconnect hardware failure is indicated, and a TRANSDUCER ALARM is sounded in block 808 and the monitor 1 brought to a STOP in block 810.

Normally block 806 is satisfied, and the inquiry as to whether the Automatic Gain Control (AGC) voltage is greater than a threshold—AGC VOLT>THRESHOLD—is made in block 812. If not, no ultrasonic pulse has as yet been received, and the transmission process is re-enabled commencing with block 802.

If a received pulse is detected in block 812, then a reasonability check on the detected delay is performed in block 814. It is therein inquired as to whether the detected change is within the physiological limits of the human subject, IS CHANGE<=PHYSIO LIMIT? In the event that it is not, process error has occurred and the transmission process is again re-enabled commencing with block 802.

If, however, all status and reasonableness checks of blocks 806, 812 and 814 are satisfied, block 816 is entered to assess whether the change in measurements dictates a rate alarm. If the measurement change does not exceed the predetermined alarm threshold, then DELTA MEAS<RATE ALARM? is answered yes and block 820 is entered. Should, however, the measurement change exceed the predetermined alarm threshold, then an ALARM is indicated in block 818.

Similarly, block 820 is entered to assess whether the absolute magnitude of the measurement dictates an alarm. If the measurement change does not exceed a predetermined alarm threshold dimension, then MEAS<DIMN ALARM? is answered yes and block 822 is entered. Should, however, the measured dimension exceed the predetermined alarm threshold dimension, then an ALARM is indicated in block 824.

Whether a dimension, or a dimensional change, has occasioned the respective ALARM of block 824, of or block 818, or not, the block 822 DISPLAY MEAS is always entered and the measurement displayed. The count number of the ultrasound transmission is thereafter reset to zero— SET N=0—in block 824, and the entire loop process re-entered at block 802.

Figure 9:
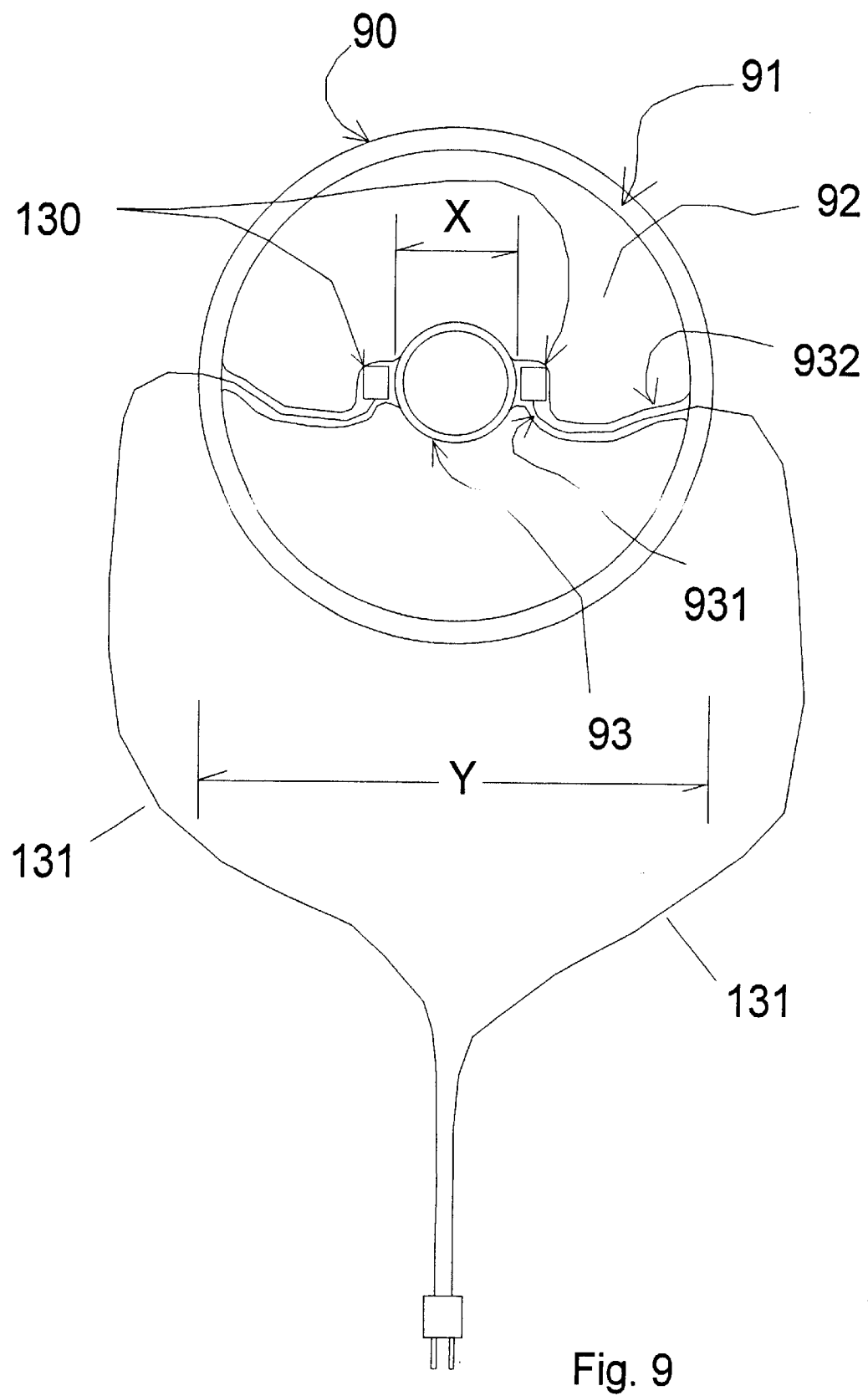
FIG. 9 is a diagrammatic perspective view of a first embodiment of a device for holding medical instrumentation sensors at and upon the cervix os of a human female in accordance with the present invention, particularly as is holding two plug-connected ultrasonic transducers of an ultrasonic transit time, real-time, cervical effacement and dilatation monitor.

The present invention concerns a particular, preferred, biomedical instrumentation probe holding system that is particularly useful with the cervical dilatation monitor described above, and with long term use of this monitor during pregnancy. A diagrammatic perspective view of a first embodiment of such a device for holding medical instrumentation sensors at and upon the cervix os of a human female in accordance with the present invention is shown in FIG. 9. The device 90 is in the substantial shape of an annular disc. It is preferably constructed entirely of surgical grade latex rubber, although the elastic modulus of the rubber used may, and desirably does, vary across the radius of the annulus, being strongest and most elastic to the exterior.

The exterior rim region 91 is normally possessed of an integral ring of substantially circular cross section and typically several millimeters diameter. The ringed rim region 91 has a shape memory. It is not appreciably subject to losing this memory over the durations and body temperatures of use, and will always be elastic to resume its original shape and circular contour.

The interior rim region 93 is likewise normally possessed of an integral ring again of substantially circular cross section and typically several millimeters diameter. This ringed rim region 93 also has a shape memory. However, this memory is not permanent, and the rim region 93 will, if held stretched indefinitely for durations in excess of days at body temperature, assume a slight "set", and become less forceful to resume its absolutely original shape and circular contour. The interior rim region 93 is, mind you, always elastic, and will when deployed at the cervix vary in size, including cyclically, with the cervix os. It is simply that, should it be called upon to expand in diameter by a factor of two or three, the interior rim region 93 will not become more and more elastically resistant to further expansion (like a rubber band) but will, in fact, exhibit about the same resistance to stretching throughout a broad range.

The interior rim region 93 is connected to the exterior rim region 91 by an elastic annulus region 92 that is typically quite thin and like onto the thin latex elastic of a condom or female diaphragm. There need be very little mechanical strength provided by this region, and its regional rupture is both uncommon (when situated in operative position) and without substantial effect on holding function of the device 90. The annulus region 92 is accordingly normally made quite less than a millimeter in thickness.

The dimension X is typically one to two centimeters (1–2 cm.), and the dimension Y four to six centimeters (4–6 cm.) as the size of the female patient wearer dictates.

One or more biomedical probes, and particularly two ultrasonic transducers 130, are held by the device 90, preferably in and by cavities 931 of complimentary shape and size located at the interior rim region 93 of the device 90. The transducers 130 are tightly permanently held and directionally disposed to point at each other across the circular central opening of the annulus. Wires 131 to each of the transducers 130 are preferably housed in integral conduits, or channels, 932 within the body of the device 90 at each of its interior rim region 93, its elastic annulus 92 and its exterior rim region 91. These integral conduits, or channels, 932 serve to direct the wires 131 at a substantial right angle to the plane of the device 90 where the wires 131 exit the exterior rim region 91. The integral conduits, or channels, 932 may alternatively direct the wires 131 to a single point on the exterior rim region 91 (not illustrated).

The wires 131 preferably terminate in a plug connector 132 that is in turn plug connected to the PINGER 115 and the RECEIVER 118 of the cervical dilatation/effacement monitor shown in block diagram in FIG. 6.

Figure 10:
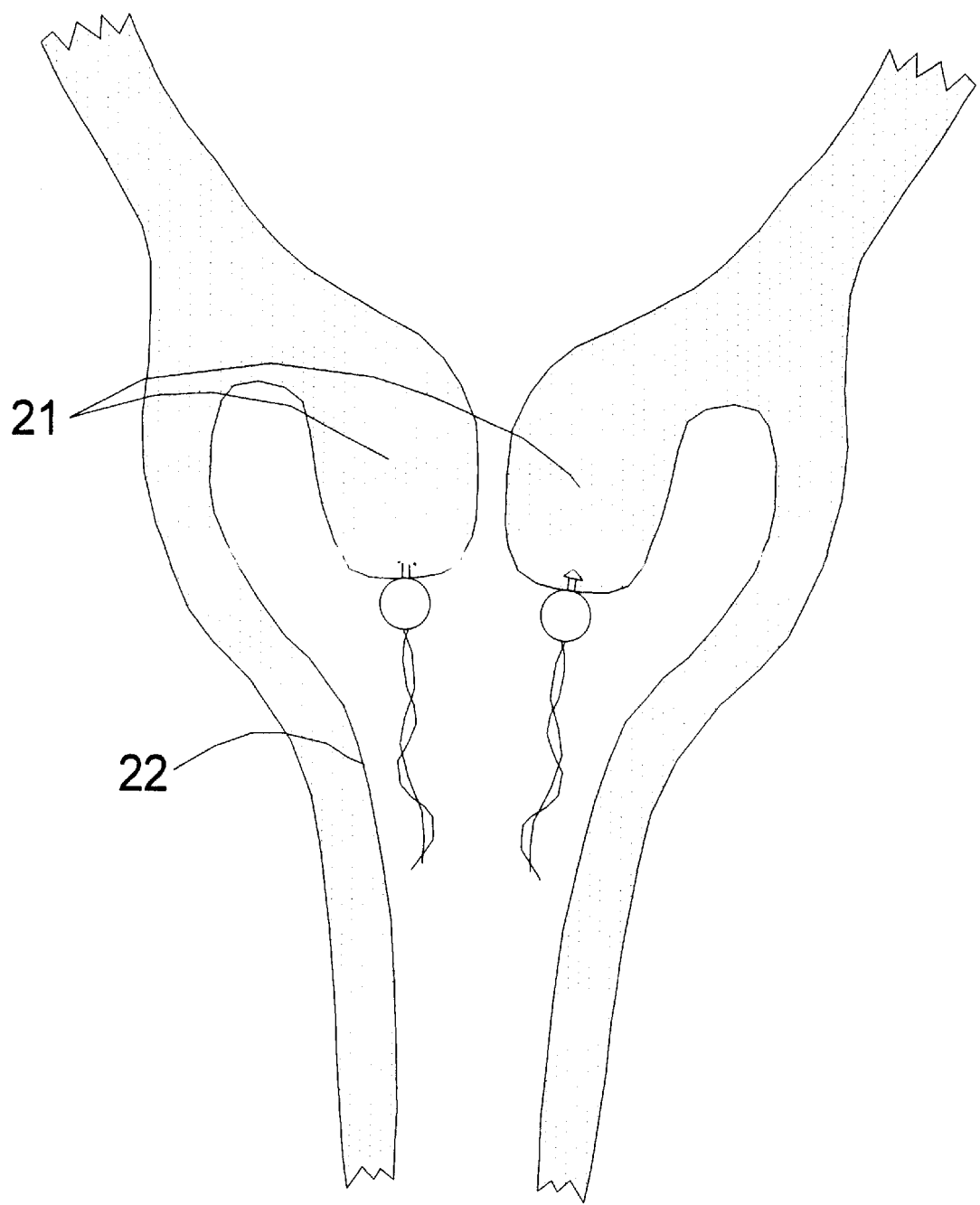
FIG. 10 is a cross-sectional plan view of the probe previously seen in FIGS. 4c–4e in position about the cervix os, and within the vaginal canal, of a human female.

A cross-sectional plan view of the probe previously seen in FIGS. 4c–4e in position about the cervix os, and within the vaginal canal, of a human female is shown in FIG. 10—primarily for ease of comparison to FIGS. 12–16. The barbed transducers 13 are hooked into the tissue of the cervix os.

Figure 11:
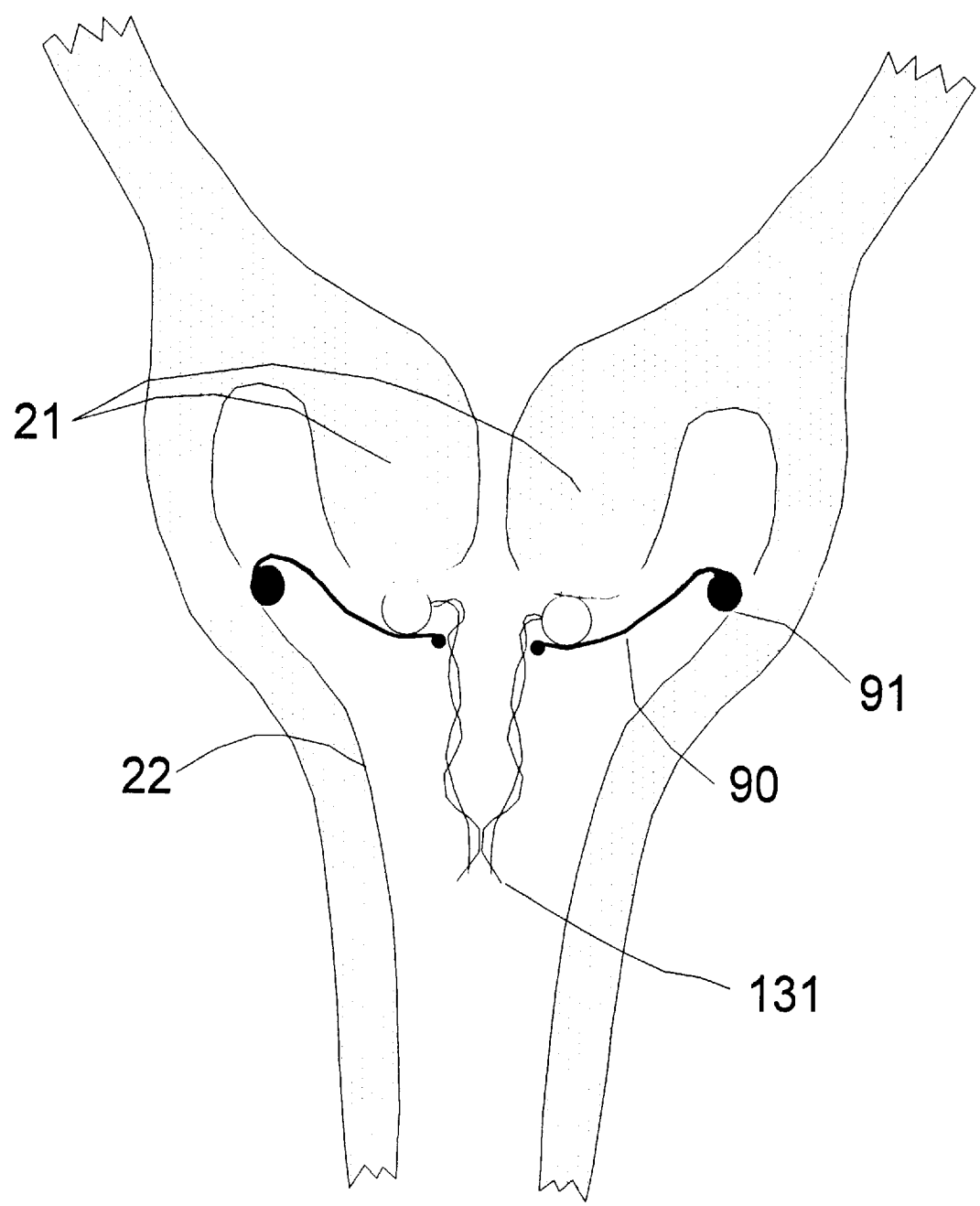
FIG. 11 is a cross-sectional plan view, similar to FIG. 10, of the first—diaphragm-like—embodiment of a holding device in accordance with the present invention previously seen in FIG. 9 in position about the cervix os, and within the vaginal canal, of a human female.

A cross-sectional plan view, similar to the view of FIG. 10, of the first—diaphragm-like—embodiment of e holding device 90 in accordance with the present invention (previously seen in FIG. 9) located in position about the cervix os, and within the vaginal canal, of a human female, is shown in FIG. 11. The exterior rim region 91 contacts and engages the interior walls of the vaginal canal 22. Probes 13a are held, as will be shown in more detail in FIG. 14.

A cross-sectional plan view of a second—cervical-cap-like—embodiment of an annular holding device 90a in accordance with the present invention is shown in FIG. 11. The second embodiment holding device 90a is retained in position by compressively embracing the cervix os.

Figure 12:
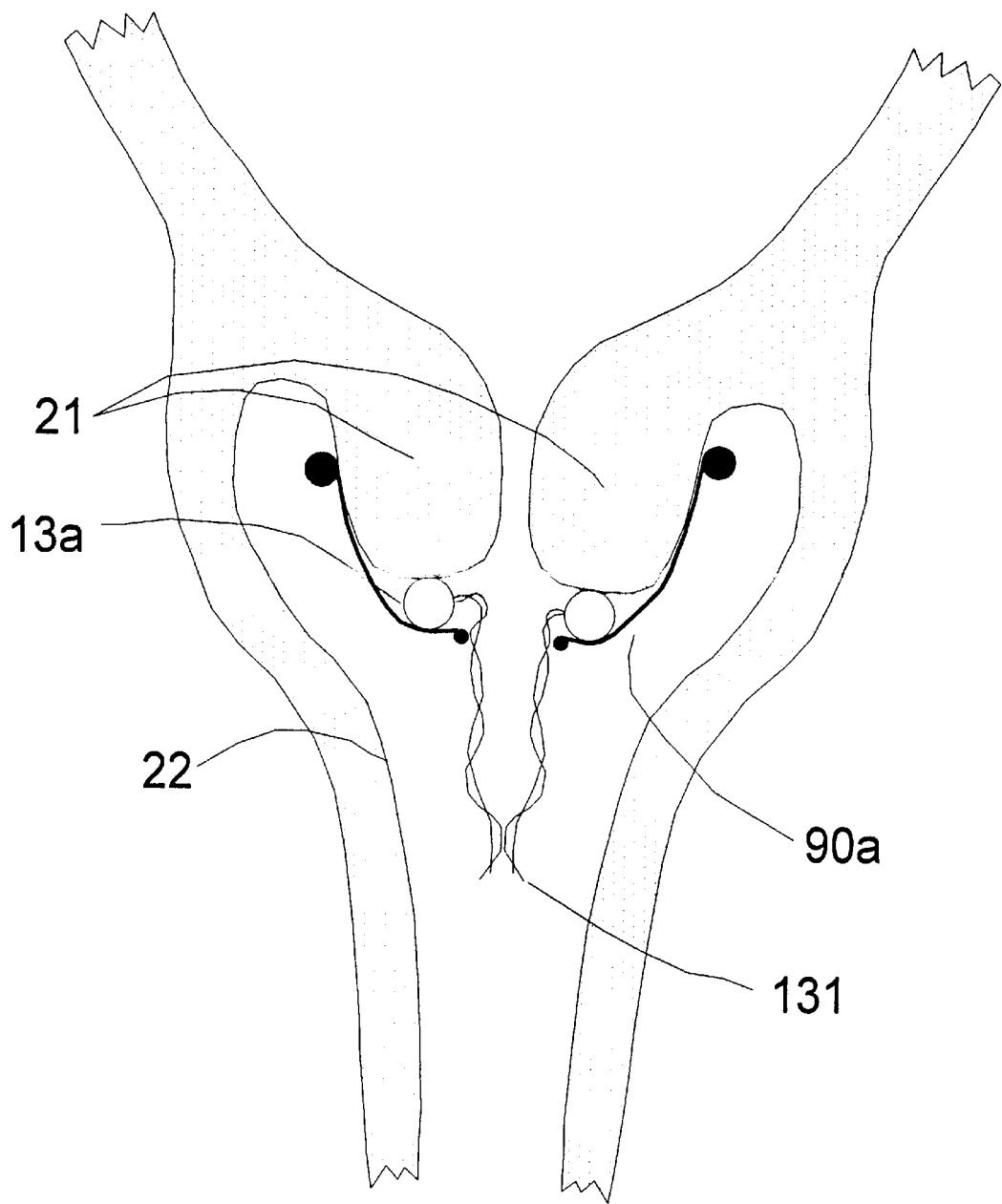
FIG. 12 is a cross-sectional plan view, similar to FIGS. 10 and 11, of a second—cervical-cap-like—embodiment of a holding device in accordance with the present invention in position about the cervix os, and within the vaginal canal, of a human female.

The cross-sectional plan view of the second embodiment of a holding device 90a in accordance with the present invention again shows the device to be in the substantial shape of planar annular disc, now shown slightly deformed in deployed position. The main difference between the embodiments is (i) size, and (ii) the tension, and elasticity, of the central annulus region 92 (shown in FIG. 9). The central annulus region 92a of the first variant 90 shown in FIG. 12 is more taught, and more tightly elastic. Either of the embodiments 90, 90a functions roughly equivalently, and equally satisfactorily, to hold position at and about the cervix os 21.

It should be understood that the ultrasonic transducers 13 (shown in FIG. 9) are not only positioned to the cervix os 21 in a relative sense, and may be or become slightly differently disposed, giving a correspondingly slightly different measured distance of separation, from time to time, and from one insertion of the device 90 to another. The precise measurement of the diameter of any one woman's cervix os is, or course, neither the requirement nor the purpose of dilatation monitoring. It is the changes, and cyclical changes, in probe separation incurred over time that are of interest, and importance, and not the absolute distance of separation of the probes. The dilatation monitor so responds, and is "self-normalizing". It is accordingly necessary only that the holding device 90 of the present invention should hold the probes stably, and to less than the deviations in cervical dimensions, over the typically several minute duration dimensional variations of labor. This the holding device 90 does. It is typically sufficient to hold the probes 13 at a constant uniform separation (the cervix os remaining constant) not varying by more than a few millimeters, if at all, during the course of one day of the wearer's normal activities.

Figure 13:
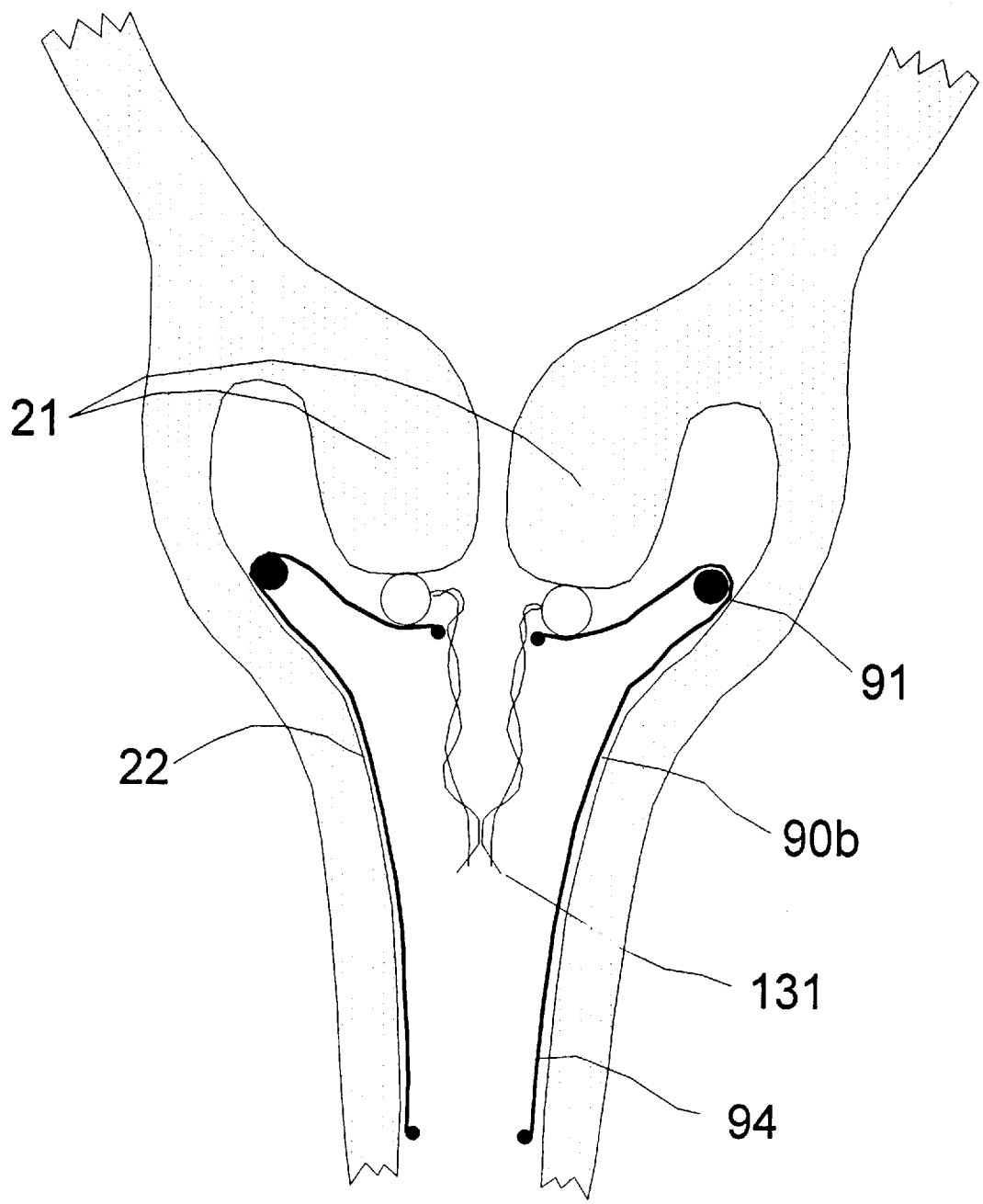
FIG. 13 is a cross-sectional plan view, similar to FIGS. 10–12, of a third—female-condom-like—embodiment of a holding device in accordance with the present invention in position about the cervix os, and within the vaginal canal, of a human female.

Yet another cross-sectional plan view, similar to FIGS. 10–12, showing a third—female-condom-like—embodiment of a holding device 90b in accordance with the present invention in position about the cervix os, and within the vaginal canal 22, of a human female, is shown in FIG. 13. The annular holding device 90b is expanded from the annular device 90 of FIG. 9 for additionally incorporating a large tube 94. The device 90b with its tube 94 is shown in deployed position about the cervix os 21 and within the vaginal canal 22, of a human female 2 (shown in FIG. 2). The tube 94 is preferably integral with the device 90b, and is an extension at and from the exterior rim region 91 (shown in FIG. 19). The region 91 is still suitably called a "rim" region, even though it not longer represents the termination of the body of the device 91, because it is of maximum diameter to the whole of the device 91, and because the tube 94 extends downwards in the vaginal canal 22 from this "rim" region 91 in the manner of female condom.

Continuing in FIG. 13, the wires 131 are desirably routed to the interior of the tube 94 where they are, quite obviously, out of contact with the wall of the vaginal canal 22. The wires normally run free inside the region of tube 94, and lower, however, and are not further sheathed in any continuation of any optional conduits, or channels 932 (shown in FIG. 9). This is so as to prevent that this narrow region should become a path for the migration of bacteria such as might cause infection.

Figure 14:
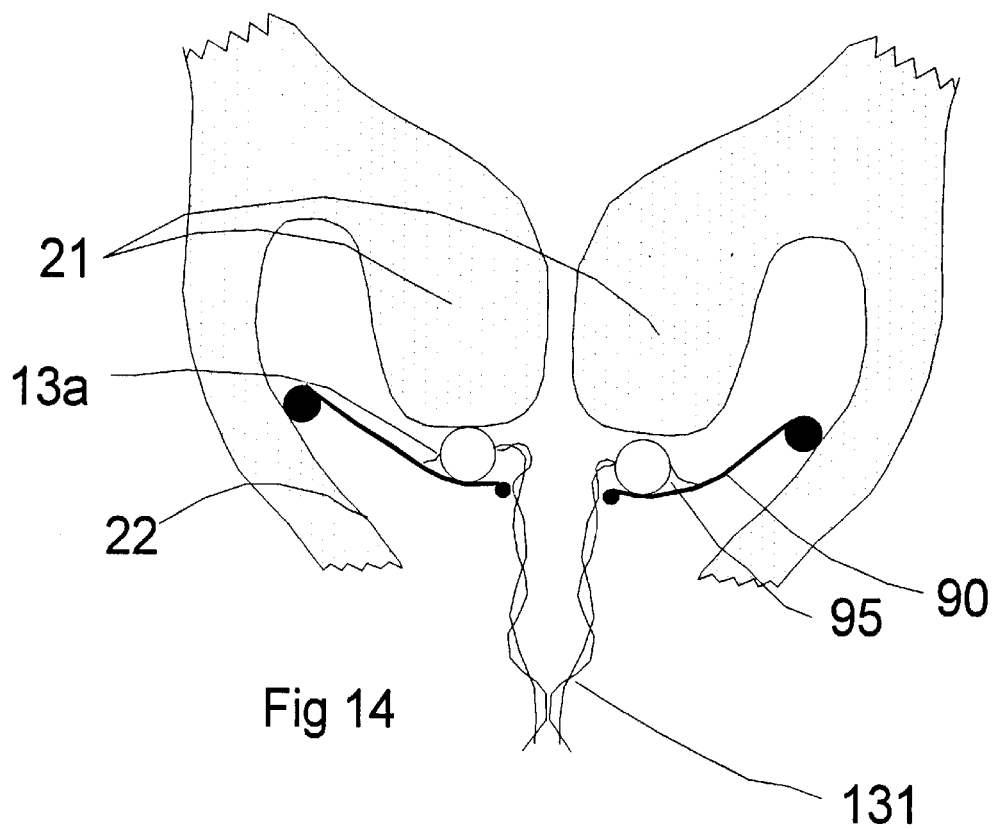
FIG. 14 is a detail cross-sectional plan view, similar to FIG. 11, of the first—diaphragm-like—embodiment of a holding device in accordance with the present invention previously seen in FIGS. 9 and 10 in position about the cervix os, and within the vaginal canal, of a human female.

A detail cross-sectional plan view, similar to FIG. 11, of the first—diaphragm-like—embodiment of a holding device 90 in accordance with the present invention is shown in FIG. 14. The device 90 holds probes 13a, normally two ultrasonic transducers, in the indicated positions about the cervix os 21, and within the vaginal canal 222, of a human female.

Figure 15:
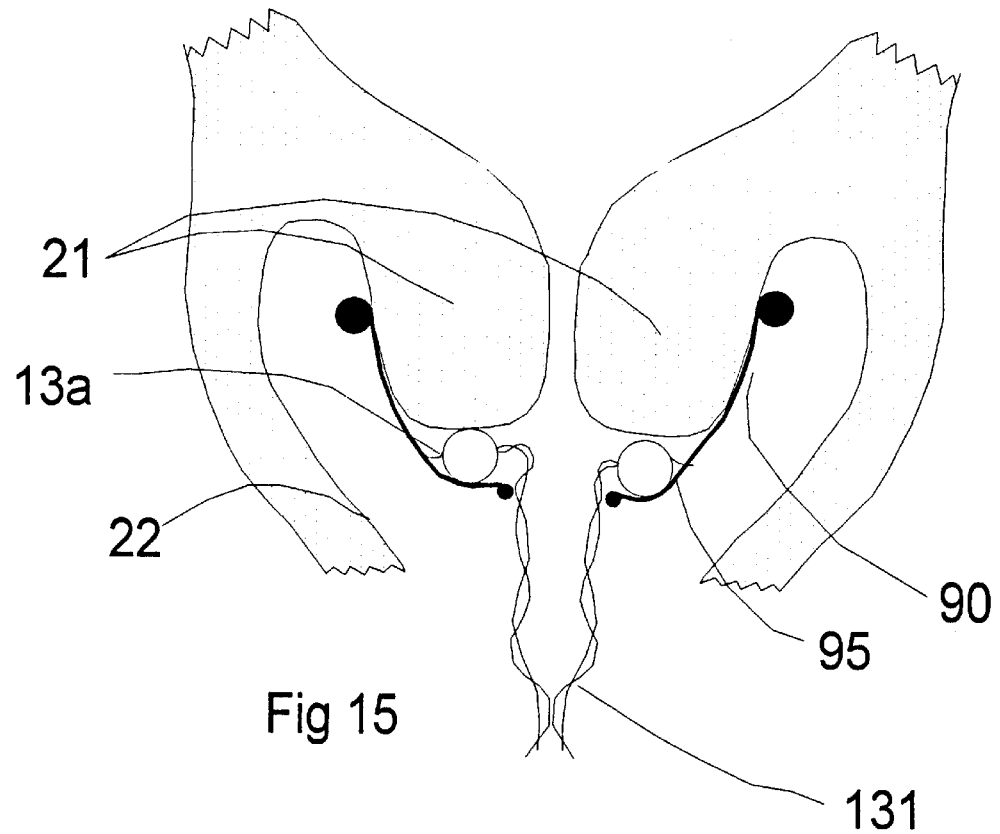
FIG. 15 is a detail cross-sectional plan view, similar to FIG. 12, of the second—cervical-cap-like—embodiment of a holding device in accordance with the present invention previously seen in FIG. 12 holding two ultrasonic transducers in first positions about the cervix os, and within the vaginal canal, of a human female.

A detail cross-sectional plan view, similar to FIG. 12, of the second—cervical-cap-like—embodiment of a holding device 90a in accordance with the present invention is shown in FIG. 15. The device 90a holds two ultrasonic transducers 13a in first positions about the cervix os 21, and within the vaginal canal 22, of a human female.

The transducers 13a need not be, however, held in the specific position illustrated in FIG. 15. A detail cross-sectional plan view of the same second—cervical-cap-like—embodiment of a holding device 90a in accordance with the present invention now holding two ultrasonic transducers 13a in second positions about the cervix os 21, and within the vaginal canal, of a human female. The rim region 91a, and the central aperture region 93a, of the second embodiment device 90a perform like functions as do the regions 91, 93 of the first embodiment device 90 illustrated in FIG. 9.

Figure 16:
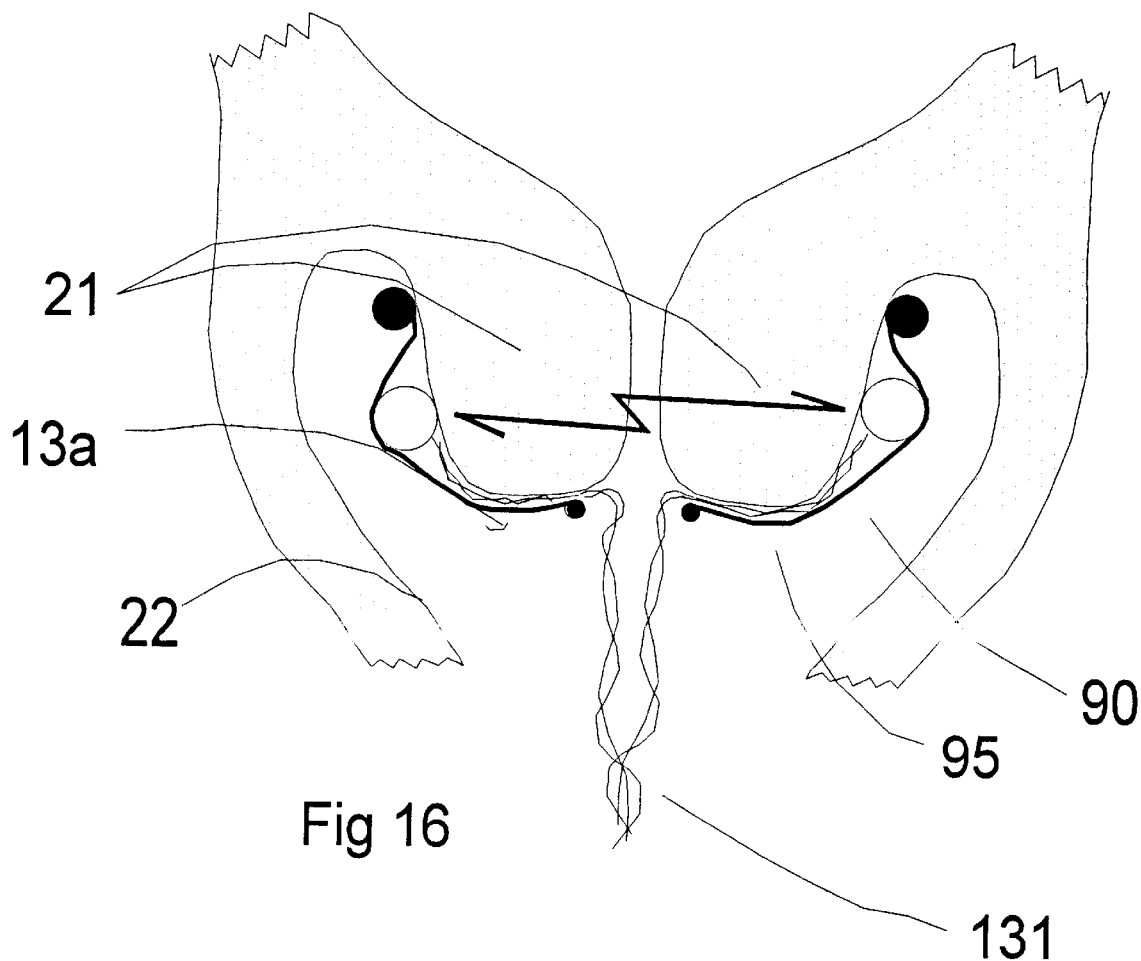
FIG. 16 is a detail cross-sectional plan view, similar to FIGS. 12 and 15, of the second—cervical-cap-like— embodiment of a holding device in accordance with the present invention previously seen in FIG. 12 and 15 holding two ultrasonic transducers in second positions about the cervix os, and within the vaginal canal, of a human female.

The probes 13 are commonly glued to surface of the holding devices 90, 90a shown in FIGS. 14–16 by non-biologically reactive adhesive 95.

Figure 17:
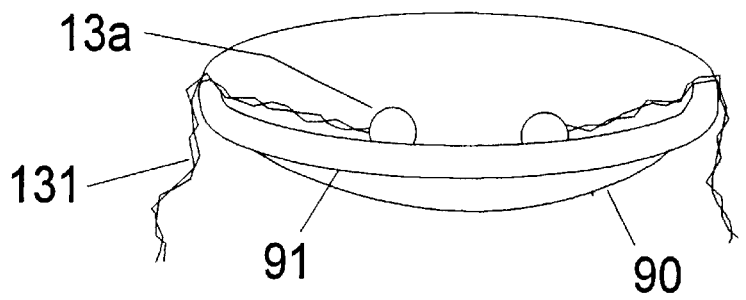
FIG. 17 is a perspective view of the first—diaphragm-like—embodiment of an annular ring holding device in accordance with the present invention with two ultrasonic transducers mounted so that their wire connections extend outboard and over the rim of the annulus.
Figure 18:
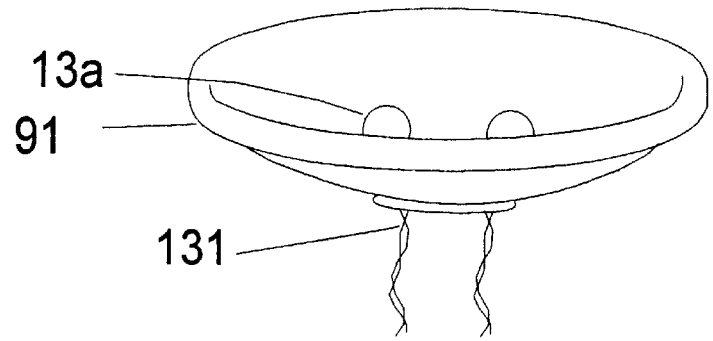
FIG. 18 is another perspective view of the first—diaphragm-like—embodiment of an annular ring holding device in accordance with the present invention previously seen in FIGS. 11, 14 and 17 now with two ultrasonic transducers mounted so that their wire connections extend through the central aperture of the annulus.

A perspective view of the first—diaphragm-like—embodiment of an annular ring holding device 90 in accordance with the present invention with two ultrasonic transducers 13a mounted so that their wire connections 131 extend outboard and over the rim region 91 of the annulus is shown in FIG. 17. Another perspective view of the same first—diaphragm-like—embodiment of an annular ring holding device 90 in accordance with the present invention now having the two ultrasonic transducers 13a mounted so that their wire connections 131 extend through the central aperture of the annulus is shown in FIG. 18.

Figure 19:
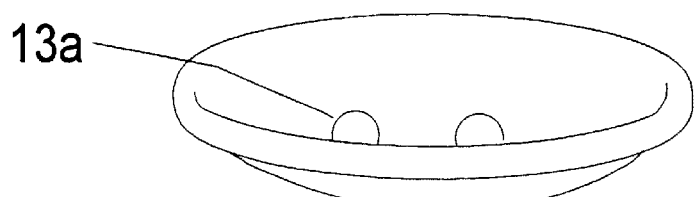
FIG. 19 is a perspective view of a variant of the first—diaphragm-like—embodiment of an annular ring holding device in accordance with the present invention previously seen in FIGS. 11, 14 where the wires of two ultrasonic transducers mounted to the holding device are sheathed in their passage through the central aperture of the annulus and away from the annulus.

A perspective view of a variant of the first—diaphragm-like—embodiment of an annular ring holding device 90 (variant) in accordance with the present invention is shown in FIG. 19. In the variant device 90 (variant) the wires of two mounted ultrasonic transducers 13a that mounted are sheathed in their passage through the central aperture of the annulus and away from the annulus by the tube 96.

Figure 20:
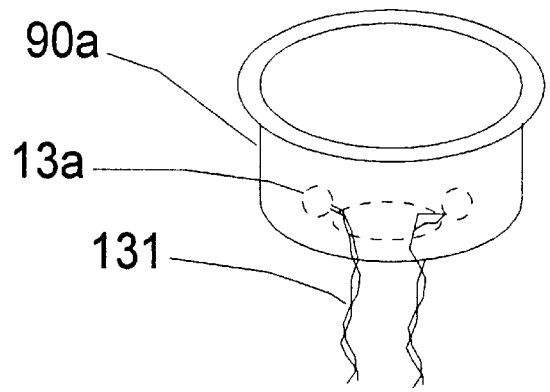
FIG. 20 is a perspective view of the second—cervical-cap-like—embodiment of an annular ring holding device in accordance with the present invention with two ultrasonic transducers mounted so that their wire connections extend through the central aperture of the annulus.

A perspective view of the second—cervical-cap-like—embodiment of an annular ring holding device 90a in accordance with the present invention is again shown in FIG. 20. Two ultrasonic transducers 13a are mounted so that their wire connections 131 extend through the central aperture of the annulus.

Figure 21:
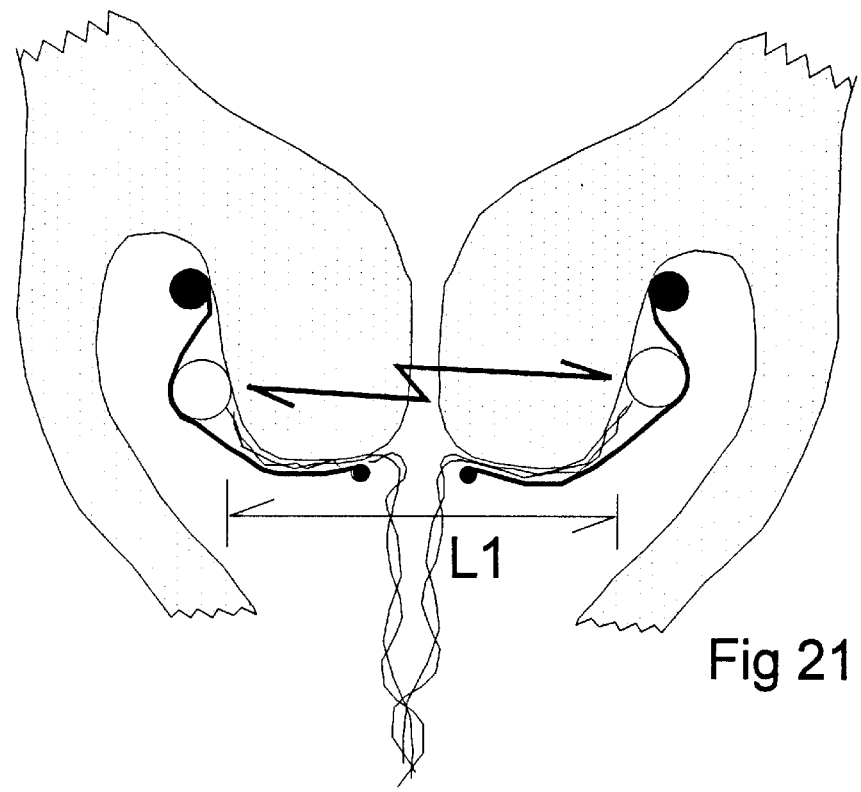
FIG. 21 is a cross-sectional view of the first—diaphragm-like—embodiment of an annular ring holding device in accordance with the present invention previously seen in FIGS. 11, 14 where the holding device and two held ultrasonic transducers mounted to the holding device are disposed on opposite sides of a cervix os that has undergone neither dilatation nor effacement.
Figure 22:
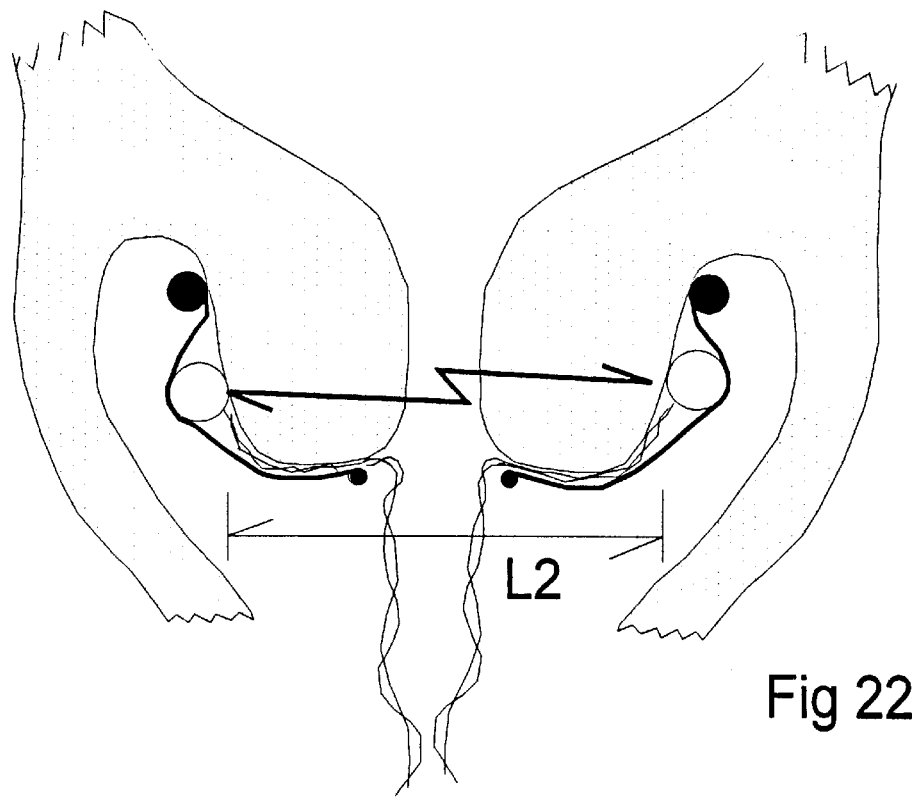
FIG. 22 is a cross-sectional view of the same first—diaphragm-like—embodiment of an annular ring holding device in accordance with the present invention previously seen in FIG. 21 where the holding device and two held ultrasonic transducers mounted to the holding device are disposed on opposite sides of a cervix os that has undergone both dilatation and effacement.

A cross-sectional view of the second—cervical-cap-like—embodiment of an annular ring holding device 90a in accordance with the present invention is again shown in FIG. 21. The two held ultrasonic transducers 13a mounted to the holding device 90a are disposed on opposite sides of a cervix os 21 that has not undergone either dilatation nor effacement. A cross-sectional view of the same second—cervical-cap-like—embodiment of an annular ring holding device 90a in accordance with the present invention previously seen in FIG. 21 is again shown in FIG. 22, only the two held ultrasonic transducers 13a mounted to the holding device 90a are disposed on opposite sides of a cervix os that has undergone both dilatation and effacement. It may be noted that the transducers 13a still hold position, as desired.

In accordance with the preceding explanation, many variations and alterations of the preferred embodiment of the present invention will suggest themselves to a practitioner of the electronic medical equipment design arts. For example, many more separate, and detailed, alarms could be made contingent upon conditions which may be quite intricate, and convolute. For example, the display, and history display, could be of alternative intervals and epochs. For example, the holding device could be intrusive into the cervix, and could also hold one or more instrumentation probes at and in contact with the walls of the womb or the placenta.

In accordance with these and other possible variations and adaptations of the present invention, the scope of the invention should be determined in accordance with the following claims, only, and not solely in accordance with that embodiment within which the invention has been taught.

What is claimed is:

1. A device for holding and retaining one or more medical instrumentation probes at and in contact with the cervix os of a human female, the device comprising:

a flexible ring means, having a shape retentive memory and exerting a force so as to assume and to maintain a predetermined closed-loop geometric shape, for, when inserted at the top of the vaginal canal and about the cervix os, holding, by its shape-retentive force, position inside and at the top of the vaginal canal and circumferentially around the cervix os; and an annulus-shaped flexible elastic membrane connected at its outer circumference to the flexible ring means so as to enshroud the cervix Os while presenting a central aperture at the cervical opening through which aperture bodily fluids may be emitted and digital examination of the cervix os may transpire, the membrane being suitably strong so as to hold one or more medical instrumentation probes as are capable of being affixed anywhere upon its surface including at the rim of the central aperture.

2. The device according to claim 1 further comprising:

a tubular membrane, having two ends, connected at a one end opening to the flexible ring means and extending downwards in the vaginal canal from the cervix os sufficiently far so that no medical instrumentation probe affixed to the annulus-shaped membrane can come into contact with the wall of the vaginal canal.

3. The device according to claim 1 for use with two ultrasonic transducer probes of an ultrasonic transit time cervimeter, the annulus-shaped flexible elastic membrane comprising:

two regions at the rim of the central aperture each of which regions is suitable to engage and to hold an ultrasonic transducer in the substantial shape of a three-dimensional, non-planar, body characterized in that ultrasound emissions from the transducer are along a multiplicity of axis in multiple different directions so that, as engaged and as held, an ultrasonic acoustic path across the opening of the cervix os is presented and enabled between two ultrasonic transducers;

wherein measurement of a transit time of ultrasound between the two transducers is an indication of the dilatation of the cervix os.

4. An ultrasonic transit time cervimeter comprising:

an ultrasonic transmitter in the substantial shape of a three-dimensional, non-planar, body characterized in that ultrasound is emitted from the transmitter along a multiplicity of axis in multiple different directions;

an ultrasonic receiver in the substantial shape of a three-dimensional, non-planar, body characterized in that ultrasound is received along a multiplicity of axis from multiple different directions;

a flexible elastomeric annulus-shaped membrane means fitting in position about the cervix os and holding the ultrasonic transmitter, and also the ultrasonic receiver, to the wall of the cervix uteri of human female at spaced apart positions so that a straight line ultrasonic acoustic path at least partially through the cervix exists between the ultrasonic transmitter and the ultrasonic receiver, the path being simultaneously along at least one ultrasound emission axis of the ultrasonic transmitter and at least one ultrasound reception axis of the ultrasonic receiver;

an ultrasonic transit time micrometer for detecting a delay in the propagation of ultrasound from the ultrasonic transmitter to the ultrasonic receiver as an indication of the dilatation of the cervix uteri; and electrical wires connecting both the ultrasonic transmitter and the ultrasonic receiver in their positions secured to the wall of the cervix by the flexible elastomeric annulus-shaped membrane means to the ultrasonic transit time micrometer.

5. The ultrasonic transit time cervimeter according to claim 4 wherein at least one of the ultrasonic transmitter and the ultrasonic receiver comprises:

an ultrasonic transducer in the substantial shape of a cylinder.

6. The ultrasonic transit time cervimeter according to claim 4 wherein at least one of the ultrasonic transmitter and the ultrasonic receiver comprises:

an ultrasonic transducer in the substantial shape of a sphere.

7. The ultrasonic transit time cervimeter according to claim 4 wherein the flexible elastomeric annulus-shaped membrane means comprises:

a flexible ring means, having a shape-retentive memory and exerting a force so as to assume and to maintain a predetermined closed-loop geometric shape, for, when inserted at the top of the vaginal canal and about the cervix os, holding, by its shape-retentive force, position inside and at the top of the vaginal canal and circumferentially around the cervix os; and an annulus-shaped flexible elastic membrane connected at its outer circumference to the flexible ring means so as to enshroud the cervix os while presenting a central aperture at the cervical opening, the membrane being suitably strong so as to hold the ultrasonic transmitter and the ultrasonic receiver upon its surface at the rim of the central aperture.

8. A method of monitoring cervical dilatation comprising:

securing an ultrasonic transmitter and an ultrasonic receiver at spaced-apart positions upon a flexible elastomeric annulus-shaped membrane;

fitting the flexible elastomeric annulus-shaped membrane in position about the cervix os so as to hold the ultrasonic transmitter, and also the ultrasonic receiver, to the wall of the cervix uteri of human female at spaced apart positions so that a straight line ultrasonic acoustic path at least partially through the cervix exists between the ultrasonic transmitter and the ultrasonic receiver;

energizing the secured ultrasonic transmitter and ultrasonic receiver with and by an ultrasonic transit time micrometer;

detecting the ultrasound propagation transit time from the ultrasonic transmitter to the ultrasonic receiver with and by use of the ultrasonic transit time micrometer in order to provide an indication of the corresponding dilatation of the cervix uteri.

9. The method of monitoring cervical dilatation according to claim 8 further comprising:

electronically monitoring the detected transit time, and the indicated dilatation of the cervix uteri corresponding to the detected transit time, in order so as to sound an alarm if a predetermined condition of dilatation is detected.

10. The method of monitoring cervical dilatation according to claim 8 wherein the electronically monitoring is of a detected transit time, and of a correspondingly indicated dilatation, that marks the onset of labor.

11. The method of monitoring cervical dilatation according to claim 8 wherein the electronically monitoring is of detected delay, and of a correspondingly indicated dilatation, that marks, once labor has commenced, the onset of problems with labor.

12. The method of monitoring cervical dilatation according to claim 8 wherein the electronically monitoring is of detected delay, and correspondingly indicated dilatation, so as mark that the dilatation of the cervix uteri has exceeded a predetermined distance.

13. The method of monitoring cervical dilatation according to claim 8 wherein the securing of the ultrasonic transmitter and the ultrasonic receiver is at spaced-apart positions between a first point upon an interior wall of the cervix uteri and a second point, the second point radially disposed radially outwardly from the first point along an extension of an imaginary vector between an imaginary central axis of the cervix uteri and the first point; and wherein the detecting is of the delay in the propagation transit time of ultrasound from the first point to the second point along an imaginary radius of the cervix uteri.

14. The method of monitoring cervical dilatation according to claim 8 wherein the securing of the ultrasonic transmitter and the ultrasonic receiver is at spaced-apart positions between two points located upon an imaginary arc segment of the wall of the cervix uteri; and wherein the detecting is of the delay in the propagation transit time of ultrasound between the two points along an imaginary arc segment of the cervix uteri.

* * * * *